(12) United States Patent
Gilliam et al.

(10) Patent No.: US 9,880,124 B2
(45) Date of Patent: Jan. 30, 2018

(54) MEASUREMENT OF ION CONCENTRATION IN PRESENCE OF ORGANICS

(71) Applicant: Calera Corporation, Los Gatos, CA (US)

(72) Inventors: Ryan J. Gilliam, San Jose, CA (US); Hong Zhao, Santa Cruz, CA (US)

(73) Assignee: Calera Corporation, Moss landing, CA (US)

( * ) Notice: Subject to any disclaimer, the term of this patent is extended or adjusted under 35 U.S.C. 154(b) by 274 days.

(21) Appl. No.: 14/937,751

(22) Filed: Nov. 10, 2015

(65) Prior Publication Data

US 2016/0131612 A1    May 12, 2016

Related U.S. Application Data

(60) Provisional application No. 62/077,810, filed on Nov. 10, 2014.

(51) Int. Cl.
| | |
|---|---|
| *G01N 27/38* | (2006.01) |
| *G01N 27/49* | (2006.01) |
| *G01N 27/28* | (2006.01) |
| *G01N 33/20* | (2006.01) |
| *G01N 27/401* | (2006.01) |

(52) U.S. Cl.
CPC .......... *G01N 27/38* (2013.01); *G01N 27/49* (2013.01); *G01N 33/20* (2013.01); *G01N 27/401* (2013.01); *Y10T 436/255* (2015.01)

(58) Field of Classification Search
CPC ...... G01N 27/38; G01N 27/401; G01N 27/49; G01N 33/20; Y10T 436/19; Y10T 436/193333; Y10T 436/200833; Y10T 436/204165; Y10T 436/21; Y10T 436/216; Y10T 436/255
USPC ......... 436/73, 77, 80, 83, 84, 124, 125, 139, 436/142, 128, 132, 149, 150, 151, 178; 422/82.01, 82.02, 69
See application file for complete search history.

(56) References Cited

U.S. PATENT DOCUMENTS

| | | | |
|---|---|---|---|
| 4,108,752 A | 8/1978 | Pohto et al. | |
| 4,111,779 A | 9/1978 | Seko et al. | |
| 4,643,818 A | 2/1987 | Seko et al. | |
| 4,959,130 A * | 9/1990 | Josowicz | G01N 27/308 204/400 |
| 7,735,274 B2 | 6/2010 | Constantz et al. | |
| 7,744,761 B2 | 6/2010 | Constantz et al. | |
| 7,749,476 B2 | 7/2010 | Constantz et al. | |

(Continued)

FOREIGN PATENT DOCUMENTS

| | | |
|---|---|---|
| EP | 2253600 A1 | 11/2010 |
| WO | WO 2008/018928 A2 | 2/2008 |

(Continued)

OTHER PUBLICATIONS

Zhang et al. Journal of Electroanalytical Chemistry, vol. 538-539, 2002, pp. 277-283.*

(Continued)

*Primary Examiner* — Maureen Wallenhorst
(74) *Attorney, Agent, or Firm* — Calera Corporation; Vandana Bansal

(57) ABSTRACT

Disclosed herein are systems and methods that relate to use of ultramicroelectrodes (UME) in measurement of ion concentration in presence of one or more organic compound(s).

20 Claims, 4 Drawing Sheets

(56) References Cited

U.S. PATENT DOCUMENTS

| | | |
|---|---|---|
| 7,753,618 B2 | 7/2010 | Constantz et al. |
| 7,754,169 B2 | 7/2010 | Constantz et al. |
| 7,771,684 B2 | 8/2010 | Constantz et al. |
| 7,790,012 B2 | 9/2010 | Kirk et al. |
| 7,815,880 B2 | 10/2010 | Constantz et al. |
| 7,829,053 B2 | 11/2010 | Constantz et al. |
| 7,875,163 B2 | 1/2011 | Gilliam et al. |
| 7,887,694 B2 | 2/2011 | Constantz et al. |
| 7,906,028 B2 | 3/2011 | Constantz et al. |
| 7,914,685 B2 | 3/2011 | Constantz et al. |
| 7,922,809 B1 | 4/2011 | Constantz et al. |
| 7,931,809 B2 | 4/2011 | Constantz et al. |
| 7,939,336 B2 | 5/2011 | Constantz et al. |
| 7,966,250 B2 | 6/2011 | Constantz et al. |
| 7,993,500 B2 | 8/2011 | Gilliam et al. |
| 7,993,511 B2 | 8/2011 | Gilliam et al. |
| 8,006,446 B2 | 8/2011 | Constantz et al. |
| 8,062,418 B2 | 11/2011 | Constantz et al. |
| 8,114,214 B2 | 2/2012 | Constantz et al. |
| 8,137,444 B2 | 3/2012 | Farsad et al. |
| 2009/0001020 A1 | 1/2009 | Constantz et al. |
| 2009/0020044 A1 | 1/2009 | Constantz et al. |
| 2009/0169452 A1 | 7/2009 | Constantz et al. |
| 2009/0202410 A1 | 8/2009 | Kawatra et al. |
| 2009/0277805 A1 | 11/2009 | Amemiya et al. |
| 2009/0293720 A1 | 12/2009 | Liu |
| 2009/0301352 A1 | 12/2009 | Constantz et al. |
| 2010/0000444 A1 | 1/2010 | Constantz et al. |
| 2010/0024686 A1 | 2/2010 | Constantz et al. |
| 2010/0051859 A1 | 3/2010 | House et al. |
| 2010/0063902 A1 | 3/2010 | Constantz et al. |
| 2010/0077691 A1 | 4/2010 | Constantz et al. |
| 2010/0077922 A1 | 4/2010 | Constantz et al. |
| 2010/0083880 A1 | 4/2010 | Constantz et al. |
| 2010/0084280 A1 | 4/2010 | Gilliam et al. |
| 2010/0108537 A1 | 5/2010 | Perego et al. |
| 2010/0111810 A1 | 5/2010 | Constantz et al. |
| 2010/0116683 A1 | 5/2010 | Gilliam et al. |
| 2010/0132556 A1 | 6/2010 | Constantz et al. |
| 2010/0132591 A1 | 6/2010 | Constantz et al. |
| 2010/0135865 A1 | 6/2010 | Constantz et al. |
| 2010/0135882 A1 | 6/2010 | Constantz et al. |
| 2010/0140103 A1 | 6/2010 | Gilliam et al. |
| 2010/0144521 A1 | 6/2010 | Constantz et al. |
| 2010/0150802 A1 | 6/2010 | Gilliam et al. |
| 2010/0154679 A1 | 6/2010 | Constantz et al. |
| 2010/0155258 A1 | 6/2010 | Kirk et al. |
| 2010/0158786 A1 | 6/2010 | Constantz et al. |
| 2010/0196104 A1 | 8/2010 | Constantz et al. |
| 2010/0200419 A1 | 8/2010 | Gilliam et al. |
| 2010/0219373 A1 | 9/2010 | Seeker et al. |
| 2010/0224503 A1 | 9/2010 | Kirk et al. |
| 2010/0229725 A1 | 9/2010 | Farsad et al. |
| 2010/0230293 A1 | 9/2010 | Gilliam et al. |
| 2010/0230830 A1 | 9/2010 | Farsad et al. |
| 2010/0236242 A1 | 9/2010 | Farsad et al. |
| 2010/0239467 A1 | 9/2010 | Constantz et al. |
| 2010/0239487 A1 | 9/2010 | Constantz et al. |
| 2010/0247410 A1 | 9/2010 | Constantz et al. |
| 2010/0258035 A1 | 10/2010 | Constantz et al. |
| 2010/0276299 A1 | 11/2010 | Kelly et al. |
| 2010/0290967 A1 | 11/2010 | Detournay et al. |
| 2010/0313793 A1 | 12/2010 | Constantz et al. |
| 2010/0313794 A1 | 12/2010 | Constantz et al. |
| 2010/0319586 A1 | 12/2010 | Blount et al. |
| 2010/0326328 A1 | 12/2010 | Constantz et al. |
| 2011/0030586 A1 | 2/2011 | Constantz et al. |
| 2011/0030957 A1 | 2/2011 | Constantz et al. |
| 2011/0033239 A1 | 2/2011 | Constantz et al. |
| 2011/0035154 A1 | 2/2011 | Kendall et al. |
| 2011/0036728 A1 | 2/2011 | Farsad et al. |
| 2011/0042230 A1 | 2/2011 | Gilliam et al. |
| 2011/0054084 A1 | 3/2011 | Constantz et al. |
| 2011/0059000 A1 | 3/2011 | Constantz et al. |
| 2011/0067600 A1 | 3/2011 | Constantz et al. |
| 2011/0067603 A1 | 3/2011 | Constantz et al. |
| 2011/0067605 A1 | 3/2011 | Constantz et al. |
| 2011/0071309 A1 | 3/2011 | Constantz et al. |
| 2011/0076587 A1 | 3/2011 | Wang et al. |
| 2011/0079515 A1 | 4/2011 | Gilliam et al. |
| 2011/0083968 A1 | 4/2011 | Gilliam et al. |
| 2011/0091366 A1 | 4/2011 | Kendall et al. |
| 2011/0091955 A1 | 4/2011 | Constantz et al. |
| 2011/0132234 A1 | 6/2011 | Constantz et al. |
| 2011/0147227 A1 | 6/2011 | Gilliam et al. |
| 2011/0203489 A1 | 8/2011 | Constantz et al. |
| 2011/0226989 A9 | 9/2011 | Seeker et al. |
| 2011/0240916 A1 | 10/2011 | Constantz et al. |
| 2011/0247336 A9 | 10/2011 | Farsad et al. |
| 2011/0277474 A1 | 11/2011 | Constantz et al. |
| 2011/0277670 A1 | 11/2011 | Self et al. |
| 2012/0292196 A1 | 11/2012 | Albrecht et al. |
| 2012/0292197 A1 | 11/2012 | Albrecht et al. |
| 2013/0206606 A1 | 8/2013 | Gilliam et al. |
| 2015/0038750 A1 | 2/2015 | Weiss et al. |

FOREIGN PATENT DOCUMENTS

| | | |
|---|---|---|
| WO | WO 2008/148055 A1 | 12/2008 |
| WO | WO 2009/006295 A2 | 1/2009 |
| WO | WO 2008/018928 A3 | 3/2009 |
| WO | WO 2009/083482 A1 | 7/2009 |
| WO | WO 2009/086460 A1 | 7/2009 |
| WO | WO 2009/006295 A3 | 12/2009 |
| WO | WO 2009/146436 A1 | 12/2009 |
| WO | WO 2009/155378 A1 | 12/2009 |
| WO | WO 2010/006242 A1 | 1/2010 |
| WO | WO 2010/008896 A1 | 1/2010 |
| WO | WO 2010/009273 A1 | 1/2010 |
| WO | WO 2010/030826 A1 | 3/2010 |
| WO | WO 2010/039903 A1 | 4/2010 |
| WO | WO 2010/039909 A1 | 4/2010 |
| WO | WO 2010/048457 A1 | 4/2010 |
| WO | WO 2010/051458 A1 | 5/2010 |
| WO | WO 2010/055152 A1 | 5/2010 |
| WO | WO 2010/068924 A1 | 6/2010 |
| WO | WO 2010/074686 A1 | 7/2010 |
| WO | WO 2010/074687 A1 | 7/2010 |
| WO | WO 2010/087823 A1 | 8/2010 |
| WO | WO 2010/091029 A1 | 8/2010 |
| WO | WO 2010/093713 A1 | 8/2010 |
| WO | WO 2010/093716 A1 | 8/2010 |
| WO | WO 2010/101953 A1 | 9/2010 |
| WO | WO 2010/104989 A1 | 9/2010 |
| WO | WO 2010/132863 A1 | 11/2010 |
| WO | WO 2010/136744 A1 | 12/2010 |
| WO | WO 2011/008223 A1 | 1/2011 |
| WO | WO 2011/017609 A1 | 2/2011 |
| WO | WO 2011/038076 A1 | 3/2011 |
| WO | WO 2011/049996 A1 | 4/2011 |
| WO | WO 2011/066293 A1 | 6/2011 |
| WO | WO 2011/075680 A1 | 6/2011 |
| WO | WO 2011/081681 A1 | 7/2011 |
| WO | WO 2011/097468 A2 | 8/2011 |
| WO | WO 2011/102868 A1 | 8/2011 |

OTHER PUBLICATIONS

International search report and written opinion dated Jan. 27, 2016 for PCT/US2015/059986.

Andersson, et al. High power diode laser cladding. Fabricating and Metalworking. Mar. 2014; 24-26.

Constantz, B. (2009) "The Risk of Implementing New Regulations on Game-Changing Technology: Sequestering CO2 in the Built Environment" AGU, 90(22), Jt. Assem, Suppl., Abstract.

Zhao, et al. Electrochemistry of high concentration copper chloride complex. Anal. Chem. 2013; 85:7696-7703.

* cited by examiner

MEASUREMENT OF ION CONCENTRATION IN PRESENCE OF ORGANICS

CROSS-REFERENCE TO RELATED APPLICATION

This application claims benefit of U.S. Provisional Patent Application No. 62/077,810, filed Nov. 10, 2014; which is incorporated herein by reference in its entirety in the present disclosure.

GOVERNMENT SUPPORT

Work described herein was made in whole or in part with Government support under Award Number: DE-FE0002472 awarded by the Department of Energy. The Government has certain rights in this invention.

BACKGROUND

In many industrial processes, real time online measurements of the concentration of the reactants and products of interest may be essential to process control. Various analytical methods including liquid or gas chromatography, mass spectrometry, spectrophotometry, and electrochemical methods have been applied. Electrochemical methods may be convenient because they can be used online and are relatively inexpensive. However most electrochemical analyses are focused on low concentrations of analyte, typically in the mM range, because of various problems like mass transfer contributions from migration and large resistive drops at M-level concentrations.

Ultramicroelectrodes (UMEs) may be a tool in electrochemical measurements in resistive solution, spatial resolution analysis, sensor for in vivo measurements, and electrode kinetics under steady state conditions. However, a need exists to measure high concentration of ions in solutions that contain organics using voltammetric techniques, such as, but not limited to, UMEs.

SUMMARY

In one aspect, there is provided a method to measure concentration of metal ions in presence of one or more organic compounds in an aqueous medium comprising:

contacting an aqueous medium comprising metal ions and one or more organic compounds with an ultramicroelectrode (UME) in a UME cell;

cleaning surface of the UME from deposition of the one or more organic compounds by passing a gas on the surface of UME, by forming a gas on the surface of UME, by mechanically cleaning the surface of UME, or combinations thereof;

subjecting the UME to a set Y of one or more potential cycles causing oxidation of the metal ions in the lower oxidation state to a higher oxidation state or causing reduction of the metal ions in higher oxidation state to a lower oxidation state; and measuring a steady state current thereby measuring the concentration of the metal ions.

In some embodiments of the above noted aspect, the measurement is of the concentration of the metal ions in the lower oxidation state when the set Y of one or more potential cycles causes the oxidation of the metal ions in the lower oxidation state to the higher oxidation state.

In some embodiments of the above noted aspect, the measurement is of the concentration of the metal ions in the higher oxidation state when the set Y of one or more potential cycles causes reduction of the metal ions in the higher oxidation state to the lower oxidation state.

In some embodiments of the above noted aspect and embodiments, the cleaning of the surface of the UME from the deposition of the one or more organic compounds by forming the gas on the surface of UME comprises subjecting the UME to a set X of one or more potential cycles to form a gas, such as, but not limited to, oxygen gas, chlorine gas, hydrogen gas, sulfur dioxide gas, or combinations thereof, on the surface of the UME. In some embodiments of the above noted aspect and embodiments, the voltage range of the set X of the one or more potential cycles is higher than reduction potential of the metal ion to prevent reduction of the metal ion and its deposition on the UME surface. In some embodiments of the above noted aspect and embodiments, the voltage range of the set X of one or more potential cycles is ±5V vs Standard Hydrogen Electrode (SHE), or ±3V vs SHE, or between 0.2V to 2.5V vs SHE, or between 0.6V to 2.5V vs SHE.

In some embodiments of the above noted aspect and embodiments, the voltage range of the set Y of the one or more potential cycles comprises oxidation or reduction potential of the metal ion or is between open circuit potential and oxidation or reduction potential of the metal ion.

In some embodiments of the above noted aspect and embodiments, the voltage range of the set Y of the one or more potential cycles comprises 0.65-0.85V vs SHE or is between open circuit potential and 0.85V vs SHE.

In some embodiments of the above noted aspect and embodiments, the metal ion is copper. In some embodiments of the above noted aspect and embodiments, the metal ion is of the metal halide, such as, but not limited to copper halide, e.g. CuCl (copper in the lower oxidation state) and $CuCl_2$ (copper in the higher oxidation state). It is to be understood that the aqueous medium comprising the metal ions may comprise metal ions in variable oxidation states or is a mixture of the metal ion in the lower oxidation state and the metal ion in the higher oxidation state. The UME in these embodiments, measures the concentration of the metal ion in the lower oxidation state when the oxidation potential is applied and the metal ion oxidizes from the lower to the higher oxidation state or the UME measures the concentration of the metal ion in the higher oxidation state when the reduction potential is applied and the metal ion reduces from the higher to the lower oxidation state. Various examples of the metal ions in the metal halide form have been provided herein.

In some embodiments of the above noted aspect and embodiments, the one or more organic compounds comprise chloroethanol and/or ethylene dichloride.

In some embodiments of the above noted aspect and embodiments, the cleaning of the surface of the UME from the deposition of the one or more organic compounds by passing the gas on the surface of the UME comprises bubbling a hydrogen gas, bubbling an oxygen gas, bubbling a nitrogen gas, or bubbling a chlorine gas on the surface of the UME.

In some embodiments of the above noted aspect and embodiments, the cleaning of the surface of the UME from the deposition of the one or more organic compounds by mechanically cleaning the surface of the UME comprises mechanically scrubbing the surface of the UME to remove the deposition.

In some embodiments of the above noted aspect and embodiments, concentration of the one or more organic compounds in the aqueous medium is between about 0.5-5000 ppm.

In some embodiments of the above noted aspect and embodiments, the one or more organic compounds are ethylene dichloride, chloroethanol, monochloroacetaldehyde, dichloroacetaldehyde, trichloroacetaldehyde, or combinations thereof.

In some embodiments of the above noted aspect and embodiments, the aqueous medium comprises more than 5 wt % water.

In some embodiments of the above noted aspect and embodiments, the UME is made of gold, platinum, titanium, carbon, conductive polymer, or iridium.

In some embodiments of the above noted aspect and embodiments, the metal ion is iron, copper, tin, chromium, or combination thereof.

In some embodiments of the above noted aspect and embodiments, the metal ion is copper. In some embodiments of the above noted aspect and embodiments, the metal ion is of metal halide. In some embodiments of the above noted aspect and embodiments, the metal ion of the metal halide is copper. In some embodiments of the above noted aspect and embodiments, the metal ion is of metal halide e.g. copper chloride. In some embodiments of the above noted aspect and embodiments, the metal ion is copper as CuCl and $CuCl_2$.

In some embodiments of the above noted aspect and embodiments, the concentration of the metal ions in the lower or the higher oxidation state is more than 0.5M or a total metal ion concentration in the aqueous medium is more than 1M; or is between 0.5-7M; or is between 0.5-6.5M; or between 1-7M; or between 1-6.5M; or between 1-6M; or between 4.5-6.5M; or between 5-6.5M.

In some embodiments of the above noted aspect and embodiments, the method further comprises subjecting the aqueous medium comprising metal ions and the one or more organic compounds to adsorption over an adsorbent before the contacting step wherein the adsorbent substantially adsorbs the one or more organic compounds from the aqueous medium.

In some embodiments of the above noted aspect and embodiments, the aqueous medium comprises less than about 5000 ppm of the one or more organic compounds after the adsorption.

In some embodiments of the above noted aspect and embodiments, the adsorbent is activated charcoal, alumina, activated silica, polymer, or combination thereof.

In some embodiments of the above noted aspect and embodiments, the adsorbent is polystyrene.

In some embodiments of the above noted aspect and embodiments, the aqueous medium is flowed through the UME to cause removal of gas bubbles on UME surface.

In some embodiments of the above noted aspect and embodiments, the flowing of the aqueous medium keeps the temperature substantially constant during the measurement.

In some embodiments of the above noted aspect and embodiments, the method further comprises keeping the UME cell at temperature of between 50-100° C.

In some embodiments of the above noted aspect and embodiments, the aqueous medium is obtained after reacting an unsaturated or saturated hydrocarbon with an anode electrolyte comprising the metal ion in the higher oxidation state in an aqueous medium, to form one or more organic compounds and the metal ion in the lower oxidation state in the aqueous medium.

In some embodiments of the above noted aspect and embodiments, the anode electrolyte comprising the metal ion in the higher oxidation state in the aqueous medium is obtained after oxidizing the metal ion from a lower oxidation state to a higher oxidation state at an anode of an electrochemical cell.

In some embodiments of the above noted aspect and embodiments, the measurement of the concentration of the metal ions in the lower and/or the higher oxidation state in the aqueous medium is conducted before, during, and/or after administration of the aqueous medium to an anode chamber of an electrochemical cell where the metal ion is oxidized from the lower oxidation state to the higher oxidation state at an anode.

In some embodiments of the above noted aspect and embodiments, the measurement of the concentration of the metal ions in the lower and/or the higher oxidation state in the aqueous medium facilitates optimization of the concentration of the metal ions in the aqueous medium before, during, and/or after its administration to the anode chamber of the electrochemical cell.

In some embodiments of the above noted aspect and embodiments, the measurement of the concentration of the metal ions in the lower and/or the higher oxidation state in the aqueous medium is conducted before, during, and/or after administration of the aqueous medium to a reactor where the metal ion in the higher oxidation state in the aqueous medium is reacted with an unsaturated or saturated hydrocarbon to form one or more organic compounds and the metal ion in the lower oxidation state in the aqueous medium.

In some embodiments of the above noted aspect and embodiments, the aqueous medium comprises metal ions in the lower as well as the higher oxidation state.

In another aspect, there is provided a method to measure concentration of copper ions in presence of one or more organic compounds in an aqueous medium comprising:

contacting an aqueous medium comprising Cu(I) ions and one or more organic compounds with an ultramicroelectrode (UME) in a UME cell;

subjecting the UME to X set of one or more potential cycles between 0.2V to 2.5V vs SHE or between 0.6V to 2.5V vs SHE and causing formation of oxygen gas, hydrogen gas, chlorine gas, or combinations thereof;

subjecting the UME to Y set of one or more potential cycles comprising 0.65-0.85V vs SHE or between open circuit potential and 0.85V vs SHE causing oxidation of the Cu(I) ions to Cu(II) ions; and measuring a steady state current thereby measuring the concentration of the Cu(I) ions in the aqueous medium.

In some embodiments of the above noted aspect, the method further comprises subjecting the aqueous medium comprising Cu(I) ions and one or more organic compounds to adsorption over an adsorbent before contacting the aqueous medium with the UME to adsorb partially or substantially the one or more organic compounds over the adsorbent.

In some embodiments of the above noted aspect and embodiments, the concentration of the one or more organic compounds in the aqueous medium after the adsorption is between about 0.5-5000 ppm.

In some embodiments of the above noted aspect and embodiments, the concentration of the Cu(I) ions in the aqueous medium is more than 0.5M or more than 1M.

In some embodiments of the above noted aspect and embodiments, the Cu(I) ions is Cu(I) halide e.g. CuCl. In some embodiments of the above noted aspect and embodiments, the Cu(II) ions is Cu(II) halide e.g. $CuCl_2$.

In another aspect, there is provided an ultramicroelectrode (UME) cell integrated with an adsorption unit, comprising: a UME cell comprising a UME configured to measure concentration of metal ions in lower and/or higher oxidation state in an aqueous medium comprising one or more organic compounds; and an adsorption unit operably connected to the UME cell comprising an adsorbent configured to adsorb the one or more organic compounds from the aqueous medium.

In some embodiments of the above noted aspect, the UME cell further comprises the aqueous medium comprising the metal ions and the one or more organic compounds.

In some embodiments of the above noted aspect, the metal ion in the lower oxidation state is copper(I).

In some embodiments of the above noted aspect and embodiments, the one or more organic compounds are ethylene dichloride, chloroethanol, monochloroacetaldehyde, dichloroacetaldehyde, trichloroacetaldehyde, or combinations thereof.

In some embodiments of the above noted aspect and embodiments, the adsorbent is activated charcoal, alumina, activated silica, polymer, or combinations thereof.

In some embodiments of the above noted aspect and embodiments, the adsorbent is polystyrene.

In some embodiments of the above noted aspect and embodiments, the adsorption unit is configured to adsorb the one or more organic compounds from the aqueous medium and deliver the aqueous medium to the UME cell.

In some embodiments of the above noted aspect and embodiments, the concentration of the one or more organic compounds in the aqueous medium after the adsorption is between 0.5 ppm-5000 ppm.

In some embodiments of the above noted aspect and embodiments, the concentration of the metal ions in the aqueous medium is more than 0.5M or more than 1M.

In some embodiments of the above noted aspect and embodiments, the UME cell and the UME have been described in detail herein.

In yet another aspect, there is provided a system configured to measure concentration of metal ions in presence of one or more organic compounds in an aqueous medium comprising: a UME cell comprising a UME configured to measure concentration of metal ions in an aqueous medium comprising one or more organic compounds; and the aqueous medium comprising metal ions and the one or more organic compounds.

In some embodiments of the above noted aspect, the UME cell further comprises a reference electrode and a salt bridge.

In some embodiments of the above noted aspect and embodiments, the system is configured for a flow-through aqueous medium.

In some embodiments of the above noted aspect and embodiments, the UME cell is fitted with compression fittings configured to withstand pressure of the flow-through aqueous medium.

In some embodiments of the above noted aspect and embodiments, the system further comprises valves configured to control flow of the aqueous medium through the UME cell.

In some embodiments of the above noted aspect and embodiments, the UME cell further comprises a temperature probe configured to monitor temperature of the aqueous medium inside the UME cell.

In some embodiments of the above noted aspect and embodiments, the UME cell further comprises a pressure probe configured to monitor pressure of the aqueous medium inside the UME cell.

In some embodiments of the above noted aspect and embodiments, the system further comprises a heating element operably connected to the UME cell and configured to heat and/or maintain the aqueous medium at a desired temperature.

In some embodiments of the above noted aspect and embodiments, the temperature of the aqueous medium in the UME cell is between 50-100° C.

In some embodiments of the above noted aspect and embodiments, the system is operably connected to an adsorption unit comprising an adsorbent configured to adsorb the one or more organic compounds from the aqueous medium and deliver the aqueous medium to the UME cell.

In some embodiments of the above noted aspect and embodiments, the concentration of the one or more organic compounds in the aqueous medium is between 0.5 ppm-5000 ppm.

In some embodiments of the above noted aspect and embodiments, the adsorbent is activated charcoal, alumina, activated silica, polymer, or combinations thereof.

In some embodiments of the above noted aspect and embodiments, the UME is made of gold, platinum, titanium, carbon, conductive polymer, or iridium.

In some embodiments of the above noted aspect and embodiments, the metal ion is iron, copper, tin, chromium, or combination thereof.

In some embodiments of the above noted aspect and embodiments, the system further comprises a reactor operably connected to the UME cell, the adsorption unit, or combination thereof and configured to react an anode electrolyte comprising metal ions in higher oxidation state with an unsaturated and/or saturated hydrocarbon to form the one or more organic compounds and the metal ions in the lower oxidation state, wherein the reactor is configured to deliver the aqueous medium comprising the one or more organic compounds and the metal ions (in the lower and higher oxidation state) to the UME cell, the adsorption unit, or combination thereof.

In some embodiments of the above noted aspect and embodiments, the system further comprises an electrochemical system comprising an anode chamber comprising an anode in contact with an anode electrolyte comprising metal ions wherein the anode is configured to oxidize the metal ions from a lower oxidation state to a higher oxidation state and wherein the electrochemical system is configured to deliver the anode electrolyte comprising the metal ions in the higher oxidation state to the reactor.

In some embodiments of the above noted aspect and embodiments, the UME cell is operably connected in-line with an outlet from the reactor and the inlet to the electrochemical system, is operably connected in-line with an outlet from the electrochemical system and the inlet to the reactor, or both.

In some embodiments of the above noted aspect and embodiments, the UME cell is operably connected to an automated control station that is configured to control operation of the system.

In some embodiments of the above noted aspect and embodiments, the UME cell is operably connected to a temperature probe configured to monitor the temperature of the aqueous medium inside the UME cell.

In some embodiments of the above noted aspect and embodiments, the system further comprises a power source operably connected to the UME cell and configured to provide voltage/current to the cell.

In some embodiments of the above noted aspect and embodiments, the power source is automated to provide various potential cycles for operation of the UME cell.

In some embodiments of the above noted aspect and embodiments, the unsaturated hydrocarbon is ethylene, the halogenated hydrocarbon is ethylene dichloride, the one or more organic compounds is chloroethanol, the metal ion is copper, or combinations thereof.

In some embodiments of the above noted aspect and embodiments, the electrochemical system further comprises a cathode chamber comprising a cathode in contact with a cathode electrolyte wherein the anode chamber and the cathode chamber are separated by an anion exchange membrane, a cation exchange membrane or both.

In some embodiments of the above noted aspect and embodiments, the UME cell is configured to subject the UME to a set Y of one or more potential cycles causing oxidation of the metal ions in lower oxidation state to a higher oxidation state or causing reduction of the metal ions in higher oxidation state to a lower oxidation state.

In some embodiments of the above noted aspect and embodiments, the UME cell is configured to clean surface of the UME from deposition of the one or more organic compounds by forming a gas on the surface of UME.

In some embodiments of the above noted aspect and embodiments, the UME cell is configured to subject the UME to a set X of one or more potential cycles to form oxygen gas, chlorine gas, hydrogen gas, sulfur dioxide gas, or combinations thereof, on the surface of the UME.

In some embodiments of the above noted aspect and embodiments, the UME cell is configured to subject the UME to a set X of one or more potential cycles to form oxygen gas, chlorine gas, hydrogen gas, sulfur dioxide gas, or combinations thereof, on the surface of the UME and the UME cell is configured to subject the UME to a set Y of one or more potential cycles causing oxidation of the metal ions in lower oxidation state to a higher oxidation state or causing reduction of the metal ions in higher oxidation state to a lower oxidation state.

In some embodiments of the above noted aspect and embodiments, the voltage range of the set Y of the one or more potential cycles comprises oxidation or reduction potential of the metal ion or is between open circuit potential and oxidation or reduction potential of the metal ion.

In some embodiments of the above noted aspect and embodiments, the voltage range of the set Y of the one or more potential cycles comprises 0.65-0.85V vs SHE or is between open circuit potential and 0.85V vs SHE.

In some embodiments of the above noted aspect and embodiments, the voltage range of the set X of one or more potential cycles is ±5V vs SHE, or ±3V vs SHE, or between 0.2V to 2.5V vs SHE, or between 0.6V to 2.5V vs SHE.

In yet another aspect, there is provided a kit, comprising: a UME cell comprising a UME configured to measure concentration of metal ions in an aqueous medium comprising one or more organic compounds. In some embodiments of the above noted aspect, the UME cell further comprises tubes, valves, pH probe, temperature probe, pressure probe, or combinations thereof. In some embodiments of the above noted aspect and embodiments, the kit further comprises an instruction manual that provides instructions or protocol on how to use the UME cell. In some embodiments of the above noted aspect and embodiments, the kit further comprises a CD, disk, or USB comprising a computer software program to operate the UME cell. In some embodiments of the above noted aspect and embodiments, the kit further comprises an adsorption unit to be operably connected to the UME cell comprising an adsorbent configured to adsorb the one or more organic compounds from the aqueous medium.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

DETAILED DESCRIPTION

Figure 1:
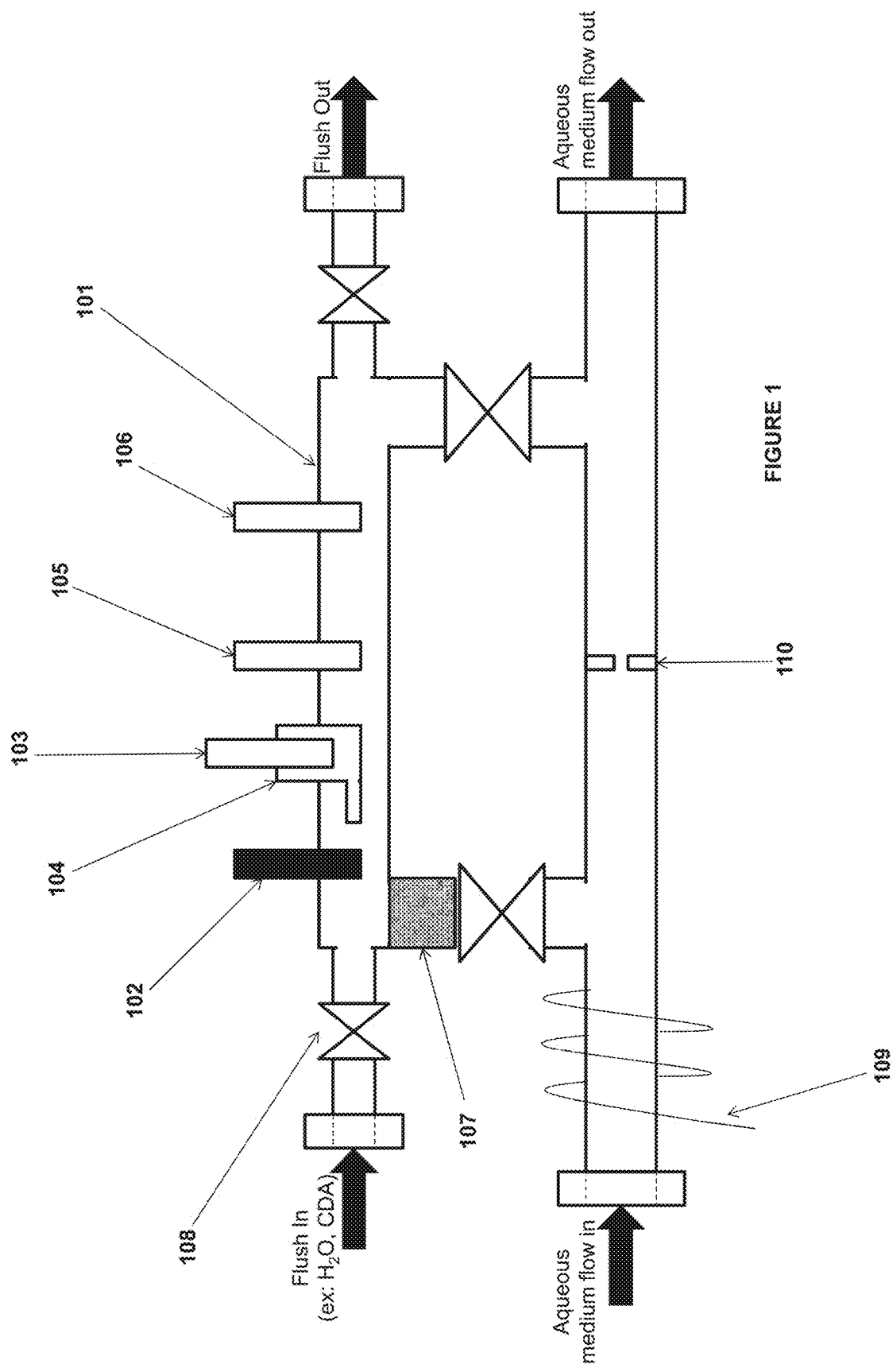
FIG. 1 is an illustration of some embodiments provided herein.

Disclosed herein are systems and methods that relate to the measurement of ion concentration, such as but not limited to, metal ion concentration using ultramicroelectrodes (UME). Traditionally, UMEs can be used to measure metal ion concentration, however, the measurement of the metal ions in the presence of organics presents a challenge. Applicants have unexpectedly and surprisingly discovered methods to measure the concentration of the ions, such as but not limited to, metal ions, in the presence of organics using UMEs.

As can be appreciated by one ordinarily skilled in the art, the present electrochemical system and method can be configured with an alternative, equivalent salt solution, e.g., an alkali metal ion solution e.g. alkali metal halide solution e.g. potassium chloride solution or sodium chloride solution or an alkaline earth metal ion solution e.g. alkaline earth metal halide solution e.g. calcium chloride solution or magnesium chloride solution or other salt solutions e.g. ammonium chloride solution. Accordingly, to the extent that such equivalents are based on or suggested by the present system and method, these equivalents are within the scope of the application.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges that are presented herein with numerical values may be construed as "about" numericals. The "about" is to provide literal support for the exact number that it precedes, as well as a number that is near to or approximately the number that the term precedes. In determining whether a number is near to or approximately a specifically recited number, the near or approximating unrequited number may be a number, which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods and Systems

There are provided methods and systems that relate to the measurement of concentration of ions, such as but not limited to, metal ions, in solution in presence of organic compounds using ultramicroelectrodes (UMEs). UMEs are typically used as a working electrode in voltammetry. The small size of UME provides relatively large diffusion layers and small currents overall. This allows UMEs to achieve steady state currents without substantial distortion. However, UMEs suffer from decaying current (rendering them useless) while measuring metal ion concentrations in the presence of organic compounds. It is contemplated that the decaying currents may be due to the deposition of organics on the surface of UMEs. Applicants discovered unique methods and systems to use UMEs to measure concentration of metal ions in aqueous solution in the presence of organic compounds.

The methods and systems described herein may be used to measure high concentration of ions, such as but not limited to, metal ions, in aqueous medium that contain one or more organic compounds. While the reference is being made to measurement of metal ions in the application, it is to be understood that any ion that can be oxidized or reduced at the UME can be measured for its concentration in the solution using the methods and systems of the invention. It is also to be understood that the metal ion may be the metal ion of any metal salt such as but not limited to, metal halide or metal sulfate etc.

The methods and systems provided herein relate to direct measurement of the concentration of electroactive metal ions by using electrochemical oxidation/reduction of the metal ions in aqueous solution in the presence of organic compounds. These methods and systems can be used in measuring and monitoring concentration of metal ions in systems where the metal ions are used in organic processes. Such processes are well known in the art and include, without limitation, organometallic processes, catalytic processes where metals are catalysts, and the like. For example, the concentration of the metal ions can be measured using the methods and systems of the invention in electrochemical systems and reactor systems described in detail in US Patent Application Publication No. 2012/0292196, filed May 17, 2012; US Patent Application Publication No. 2013/0206606, filed Mar. 13, 2013; and US Patent Application Publication No. 2015/0038750, filed Jul. 30, 2014, all of which are incorporated herein by reference in their entireties in the present disclosure.

Described herein below are UME and its components, UME cells and its components, systems comprising UME and its components, and method protocols to use UME to measure concentration of the metal ions.

UME, UME Cell, Systems, and Components

In one aspect, there is provided a UME cell comprising: a UME configured to measure concentration of metal ions in an aqueous medium comprising one or more organic compounds. In some embodiments, there is provided a UME cell comprising: a UME configured to measure concentration of metal ions in an aqueous medium comprising one or more organic compounds; and the aqueous medium comprising the metal ions and the one or more organic compounds. The measurement may be of the metal ion in the lower oxidation state and/or the metal ion in the higher oxidation state. In some embodiments, there is provided a method, comprising: providing an aqueous medium comprising metal ions and one or more organic compounds to a UME cell comprising a UME; and using the UME cell to measure concentration of the metal ions in the aqueous medium. The method protocols for the measurement have been described in detail herein.

The "UME" as used herein includes an electrode that has at least one dimension smaller than 30 um (microns). For example only, the UME may have at least one dimension between 0.1-30 um. The UME may be made of any conventional conductive electrode material including, but not limited to, gold, platinum, titanium, carbon, iridium, conductive polymer, and the like.

The "UME cell" as used herein includes a cell comprising the UME and other components such as reference electrode, for example, but not limited to, Ag|AgCl reference electrode. The "reference electrode" as used herein includes any electrode that has a known electrode potential. Various reference electrodes are known in the art and are all are within the scope of the invention. Examples of reference electrodes include, without limitation, aqueous reference electrodes such as standard hydrogen electrode (SHE), normal hydrogen electrode, reversible hydrogen electrode, saturated calomel electrode, copper-copper (II) sulfate electrode, silver chloride electrode, pH-electrode, palladium-hydrogen electrode, or dynamic hydrogen electrode, etc. Examples of reference electrodes also include, without limitation, non-aqueous reference electrodes, a quasi-reference electrode, a pseudo-reference electrode, etc. The reference electrode potentials may differ from each other. For example, 0.45V vs. Ag|AgCl is same as about 0.65V vs. SHE, or −1V vs. Ag|AgCl is same as about −0.8V vs. SHE etc.

In some embodiments, the UME cell may optionally contain a counter electrode or an auxiliary electrode. The "counter electrode" or "auxiliary electrode" as used herein includes any electrode that is used in a three electrode electrochemical cell in which current is expected to flow. The counter or auxiliary electrode may be fabricated from electrochemically inert materials such as gold, platinum, or carbon etc.

In some embodiments, the UME cell may optionally contain a salt bridge, an ion exchange membrane, or the like. The "salt bridge" as used herein is a bridge used to connect the oxidation and reduction half cells in an electrochemical cell. The salt bridge may be a glass tube bridge, a filter paper bridge, etc. In some embodiments of the systems provided herein, the salt bridge is filled with an inert electrolyte, such as, but not limited to, sodium chloride or potassium chloride. In some embodiments of the systems provided herein, the salt bridge is filled with a concentrated salt or saturated salt solution. In some embodiments, it may be beneficial to provide saturated salt in the salt bridge in order to prevent precipitation of ions in the salt bridge.

In some embodiments, the UME cell may further comprise a temperature probe configured to monitor temperature of the aqueous medium inside the UME cell, such as a thermocouple. In some embodiments, the UME cell may further comprise a pressure probe configured to monitor pressure of the aqueous medium inside the UME cell. In addition to measuring pressure, the pressure probes may also be used to measure fluid/gas flow, speed, water level, altitude, leak, etc. In some embodiments, the UME cell may further comprise a pH probe configured to monitor pH of the aqueous medium inside the UME cell. The pH probe may be a pH meter for measuring the pH of the aqueous medium. In some embodiments, the UME cell may further comprise a TOC (Total Organic Carbon) meter configured to monitor the concentration of the one or more organic compounds in the aqueous medium inside the UME cell. The UME cell may be fitted with one or more of the foregoing probes as desired.

In some embodiments, the UME cell is configured for a flow-through aqueous medium. In some embodiments, the UME cell and/or its components are fitted with compression fittings configured to withstand pressure of the flow-through aqueous medium.

The "metal ion" or "metal" as used herein, includes any metal ion capable of being converted from lower oxidation state to higher oxidation state or vice versa. Examples of metal ions include, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combinations thereof. In some embodiments, the metal ions include, but not limited to, iron, copper, tin, chromium, or combination thereof. In some embodiments, the metal ion is copper. In some embodiments, the metal ion is tin. In some embodiments, the metal ion is iron. In some embodiments, the metal ion is chromium. In some embodiments, the metal ion is platinum. The "oxidation state" as used herein, includes degree of oxidation of an atom in a substance. For example, in some embodiments, the oxidation state is the net charge on the ion. As used herein "lower oxidation state" includes the lower oxidation state of the metal. For example, lower oxidation state of the metal ion may be 1+, 2+, 3+, 4+, or 5+. As used herein "higher oxidation state" includes the higher oxidation state of the metal. For example, higher oxidation state of the metal ion may be 2+, 3+, 4+, 5+, or 6+. Some examples of the metal ions and their oxidation or reduction potential are provided in Tables 1 and 2 herein.

The metal ion may be present in the aqueous medium as a compound or salt of the metal or an alloy of the metal or combination thereof. In some embodiments, the anion attached to the metal ion is a halide e.g. chloride, such as, but not limited to, iron chloride, copper chloride, tin chloride, chromium chloride etc. is used as the metal compound. In some embodiments, the anion attached to the metal is a sulfate, such as, but not limited to, iron sulfate, copper sulfate, tin sulfate, chromium sulfate etc. is used as the metal compound. In some embodiments, the anion attached to the metal is a halide e.g. bromide, such as, but not limited to, iron bromide, copper bromide, tin bromide etc. is used as the metal compound. Similarly, iodide or fluoride may also be used as a halide in the metal halide.

Some examples of the metal compounds that may be measured in the systems and methods of the invention include, but are not limited to, copper (II) sulfate, copper (II) nitrate, copper (I) chloride, copper (II) chloride, copper (I) bromide, copper (II) bromide, copper (I) iodide, copper (II) iodide, iron (III) sulfate, iron (III) nitrate, iron (II) chloride, iron (II) bromide, iron (II) iodide, tin (II) sulfate, tin (II) nitrate, tin (II) chloride, tin (IV) chloride, tin (II) bromide, tin (II) iodide, chromium (III) sulfate, chromium (III) nitrate, chromium (II) chloride, chromium (II) bromide, chromium (II) iodide, zinc (II) chloride, zinc (II) bromide, etc.

The "one or more organic compounds" or "organic compound" or "organic products" as used herein, include any compound that has carbon in it. Examples include without limitation any hydrocarbon such as alkane, alkene, or alkyne, cyclic ring (aliphatic or aromatic), or derivatives thereof. Examples of alkane, alkene, or alkyne etc. include, without limitation, ethylene, ethane, propylene, propane, butylene, butane, pentylene, pentane etc. For example only, derivatives of alkanes, alkene, or alkynes include halogenated alkanes, halogenated alkenes, or halogenated alkynes; hydroxyl substituted alkanes, hydroxyl substituted alkenes, or hydroxyl substituted alkynes; sulfo substituted alkanes, sulfo substituted alkenes, or sulfo substituted alkynes; aldehyde substituted alkanes, aldehyde substituted alkenes, or aldehyde substituted alkynes; or combinations thereof. The organic compound may be the halohydrocarbon or sulfohydrocarbon described in detail herein. For example, the one or more organic compounds include, without limitation, ethylene dichloride, chloroethanol, chloropropene, propylene oxide, allyl chloride, methyl chloride, 1,1,2-trichloroethane, 1,1,2,2-tetrachloroethane, pentachloroethane, 1,1-dichloroethene, trichloroethylene, tetrachloroethene, chloral ($CCl_3CHO$) and/or chloral hydrate (2,2,2-trichloroethane-1, 1-diol), propane dichloride ($C_3H_6Cl_2$) or dichloropropane (DCP), butane dichloride ($C_4H_8Cl_2$) or dichlorobutene ($C_4H_6Cl_2$), chlorobutanol, chlorobenzene, chlorophenol, chlorinated toluene, chloroacetylene, dichloroacetylene, vinyl chloride, etc.

The "aqueous medium" used herein includes a medium that contains more than 1 wt % water. In some embodiments, the aqueous medium includes more than 5 wt % water; or more than 5.5 wt % water; or more than 6 wt %; or more than 20 wt % water; or more than 50 wt % water; or more than 80 wt % water; or more than 90 wt % water; or between 5-90 wt % water; or between 5-70 wt % water; or between 5-50 wt % water; or between 5-20 wt % water; or between 5-10 wt % water; or between 6-90 wt % water; or between 6-50 wt % water; or between 6-10 wt % water; or between 10-75 wt % water; or between 10-50 wt % water; or between 20-60 wt % water; or between 20-50 wt % water; or between 25-60 wt % water; or between 25-50 wt % water; or between 25-45 wt % water; or between 40-60 wt % water; or between 40-50 wt % water; or between 50-75 wt % water; or between 50-60 wt % water; or between 60-70 wt % water. In some embodiments, the aqueous medium may comprise a water soluble organic solvent. Such organic solvents are well known in the art.

In the aspects and embodiments described herein, the concentration of the one or more organic compounds in the aqueous medium in the UME cell is between 0.5 ppm-5000 ppm. In some embodiments, the concentration of the one or more organic compounds in the aqueous medium in the UME cell is between 0.5 ppm-5000 ppm; or between 0.5 ppm-4000 ppm; or between 0.5 ppm-3000 ppm; or between 0.5 ppm-2000 ppm; or between 0.5 ppm-1000 ppm; or between 0.5 ppm-800 ppm; or between 0.5 ppm-600 ppm; or between 0.5 ppm-500 ppm; or between 0.5 ppm-400 ppm; or between 0.5 ppm-300 ppm; or between 0.5 ppm-200 ppm; or between 0.5 ppm-100 ppm; or between 0.5 ppm-50 ppm; or between 0.5 ppm-10 ppm; or between 5 ppm-5000 ppm; or between 5 ppm-4000 ppm; or between 5 ppm-3000 ppm; or between 5 ppm-2000 ppm; or between 5 ppm-1000 ppm; or between 5 ppm-800 ppm; or between 5 ppm-600 ppm; or between 5 ppm-500 ppm; or between 5 ppm-400 ppm; or between 5 ppm-300 ppm; or between 5 ppm-200 ppm; or between 5 ppm-100 ppm; or between 5 ppm-50 ppm; or between 5 ppm-10 ppm; or between 10 ppm-5000 ppm; or between 10 ppm-4000 ppm; or between 10 ppm-3000 ppm; or between 10 ppm-2000 ppm; or between 10 ppm-1000 ppm; or between 10 ppm-800 ppm; or between 10 ppm-600 ppm; or between 10 ppm-500 ppm; or between 10 ppm-400 ppm; or between 10 ppm-300 ppm; or between 10 ppm-200 ppm; or between 10 ppm-100 ppm; or between 10 ppm-50 ppm; or between 50 ppm-600 ppm; or between 100 ppm-600 ppm; or between 200 ppm-600 ppm; or between 400 ppm-600 ppm.

In the aspects and embodiments described herein, the metal ion in the aqueous medium is in a high concentration, higher than typically measured by the UME. In the aspects and embodiments described herein, the total metal ion concentration (the metal ion in the lower and the higher oxidation state) is more than 0.5M; or more than 1M; or between about 0.5-8M; or between about 0.5-7M; or between about 0.5-6M; or between about 0.5-5M; or between about 0.5-4M; or between about 0.5-3M; or between about 0.5-2M; or between about 0.5-1.5M; or between about 0.5-1M; or between about 0.5-0.8M; or between about 0.8-8M; or between about 0.8-7M; or between about 0.8-6M; or between about 0.8-5M; or between about 0.8-4M; or between about 0.8-3M; or between about 0.8-2M; or between about 0.8-1.5M; or between about 0.8-1M; or between about 1-8M; or between about 1-7M; or between about 1-6M; or between about 1-5M; or between about 1-4M; or between about 1-3M; or between about 1-2M; or between about 1-1.5M; or between about 2-8M; or between about 2-7M; or between about 2-6M; or between about 2-5M; or between about 2-4M; or between about 2-3M; or between about 3-8M; or between about 3-7M; or between about 3-6M; or between about 3-5M; or between about 3-4M; or between about 4-8M; or between about 4-7M; or between about 4-6M; or between about 4-5M; or between about 5-8M; or between about 5-7M; or between about 5-6M; or between about 6-8M; or between about 6-7M; or between about 7-8M. In some embodiments, the foregoing metal ion concentrations further include salt concentrations in the aqueous medium, such as but not limited to alkali metal halide (for example only, sodium chloride, potassium chloride, etc.) or alkaline earth metal halide (for example only, calcium chloride, magnesium chloride, etc.) in concentration of between 0.1-5M; or between 0.1-4M; or between 0.1-3M; or between 0.1-2M; or between 0.1-1M; or between 1-5M; or between 1-4M; or between 1-3M; or between 1-2M; or between 2-5M; or between 2-4M; or between 2-3M; or between 3-5M; or between 3-4M; or between 4-5M. In some embodiments of the aspects and embodiments provided herein, the concentration of the metal ion in the lower oxidation state is between 0.5-2.5M; or between 0.5-2M; or between 0.5-1.5M; or between 0.5-1M; and the concentration of the metal ion in the higher oxidation state is between 4-7M; or between 4-6.5M; or between 4-6M; or between 4-5M; or between 5-7M; or between 5-6.5M; or between 5-6M; or between 6-7M, in the aqueous medium. In some embodiments of the foregoing embodiment, the concentration of the salt such as alkali metal halide e.g. sodium chloride is between 1.5-3M in the aqueous medium.

In some embodiments of the aspects and embodiments provided herein, the concentration of the one or more organic compounds in the aqueous medium can be reduced by adsorbing the one or more organic compounds over an adsorbent before measuring the concentration of the metal ions in the aqueous medium using the UME. Accordingly, in some embodiments, the systems provided herein comprise the UME cell as described herein operably connected to an adsorption unit that is configured to adsorb the one or more organic compounds from the aqueous medium and deliver the aqueous medium to the UME cell. In some embodiments, the adsorption unit comprises an adsorbent. In some embodiments, the adsorbent substantially adsorbs, e.g. adsorbs more than 90 wt %, or up to 90 wt %, or up to 95 wt %, or up to 99 wt %, of the one or more organic compounds from the aqueous medium.

The "adsorbent" as used herein includes a compound that has a high affinity for the organic compounds and none or very low affinity for the metal ions. In some embodiments, the adsorbent does not have or has very low affinity for water in addition to none or low affinity for metal ions. Accordingly, the adsorbent may be a hydrophobic compound that adsorbs organics but repels metal ions and water.

In some embodiments, the adsorbents include, but not limited to, activated charcoal, alumina, activated silica, polymers, etc., to remove the organic compounds from the metal ion solution. These adsorbents are commercially available. Examples of activated charcoal that can be used in the methods include, but not limited to, powdered activated charcoal, granular activated charcoal, extruded activated charcoal, bead activated carbon, impregnated carbon, polymer coated carbon, carbon cloth, etc. The "adsorbent polymers" or "polymers" used in the context of the adsorbent herein includes polymers that have high affinity for organic compounds but none or low affinity for metal ions and water. Examples of polymer that can be used as adsorbent include, but not limited to, polyolefins. The "polyolefin" or "polyalkene" used herein includes a polymer produced from an olefin (or an alkene) as a monomer. The olefin or the alkene may be an aliphatic compound or an aromatic compound. Examples include, but not limited to, polyethylene, polypropylene, polystyrene, polymethylpentene, polybutene-1, polyolefin elastomers, polyisobutylene, ethylene propylene rubber, polymethylacrylate, poly(methylmethacrylate), poly(isobutylmethacrylate), and the like.

In some embodiments, the adsorbent used herein substantially adsorbs, e.g. more than 90% w/w organic compounds; more than 95% w/w organic compounds; or more than 99% w/w; or more than 99.99% w/w organic compounds; or more than 99.999% w/w organic compounds, from the aqueous medium containing metal ions, organic compounds, and water. In some embodiments, the adsorbent used herein adsorbs less than 2% w/w metal ions; or less than 1% w/w metal ions; or less than 0.1% w/w metal ions; or less than 0.01% w/w metal ions; or less than 0.001% w/w metal ions from the aqueous medium containing metal ions, organic compounds, and water. In some embodiments, the adsorbent used herein does not adsorb metal ions from the aqueous medium.

In some embodiments, the aqueous medium obtained after passing through the adsorbent (and that is circulated to the UME cell) contains less than 5000 ppm, or less than 1000 ppm, or less than 800 ppm, or less than 700 ppm, or less than 600 ppm, or less than 500 ppm, or less than 250 ppm, or less than 100 ppm, or less than 50 ppm, or less than 10 ppm, or less than 1 ppm, or the other various concentrations described herein, of the organic compound.

The adsorbent may be used in any shape and form available commercially. For example, in some method and system embodiments, the adsorbent is a powder, plate, mesh, beads, cloth, fiber, pills, flakes, blocks, and the like. In some method and system embodiments, the adsorbent is in the form of a bed, a packed column, and the like. In some method and system embodiments, the adsorbent may be in the form of series of beds or columns of packed adsorbent material. For example, in some method and system embodiments, the adsorbent is one or more of packed columns (arranged in parallel or in series) containing activated charcoal powder, polystyrene beads or polystyrene powder.

In some embodiments, the system comprising the UME cell is constructed in such a way that the adsorption unit is integrated with the UME cell. In some embodiments, the system comprising the UME cell is constructed in such a way that the adsorption unit is operably attached to the UME cell but can be separated from the UME cell with ease for regeneration purposes. In some embodiments, the system comprising the UME cell is constructed in such a way that the adsorption unit is a cartridge or the like that can be attached or detached from the UME cell at will for cleaning and regeneration purposes.

In some embodiments, the adsorption unit may be detachable (e.g. in a form of cartridge) from the UME cell or the system comprising the UME cell such that the adsorbent may be regenerated after several uses. In some method and system embodiments, the adsorbent is regenerated after the adsorption of the organic products by using various desorption techniques including, but not limited to, purging with an inert fluid (such as water), change of chemical conditions such as pH, increase in temperature, reduction in partial pressure, reduction in the concentration, purging with inert gas at high temperature, such as, but not limited to, purging with steam, nitrogen gas, argon gas, or air at >100° C., etc.

In some method and system embodiments, the adsorbent may be disposed, burnt, or discarded after the desorption process. In some method and system embodiments, the adsorbent is reused in the adsorption process after the desorption. In some method and system embodiments, the adsorbent is reused in multiple adsorption and regeneration cycles before being discarded. In some method and system embodiments, the adsorbent is reused in one, two, three, four, five, or more adsorption and regeneration cycles before being discarded.

In another aspect, there is provide a system configured to measure concentration of metal ions in presence of one or more organic compounds in an aqueous medium comprising: a UME cell described herein. There is provided a system configured to measure concentration of metal ions in presence of one or more organic compounds in an aqueous medium comprising: a UME cell comprising a UME configured to measure concentration of metal ions in an aqueous medium comprising one or more organic compounds. There is also provided a system configured to measure concentration of metal ions in presence of one or more organic compounds in an aqueous medium comprising: a UME cell comprising a UME configured to measure concentration of metal ions in an aqueous medium comprising one or more organic compounds and an adsorption unit operably connected to the UME cell comprising an adsorbent configured to adsorb the one or more organic compounds from the aqueous medium. In some embodiments of the foregoing systems, the system further comprises the aqueous medium comprising the metal ions in lower and/or higher oxidation state and the one or more organic compounds. The UME cell and its components and the adsorption unit, all have been described herein above. In some embodiments of the system, the system is configured for flow-through aqueous medium. In some embodiments, the system further comprises valves configured to control flow of the aqueous medium through the UME cell. The valves around the UME cell and the compression fitting of the components in the UME cell facilitate the flow-through system of the aqueous medium in the UME cell thereby providing effective measurement of the concentration of the metal ions.

In some embodiments of the system, the system is configured with a heating element operably connected to the UME cell or at any other place in the system and configured to heat and/or maintain the aqueous medium at a desired temperature. The heating element may be heat tape, heat coil, liquid jacketing, insulation, etc. In some embodiments of the system, the temperature of the aqueous medium in the UME cell is between 50-100° C.; or between 60-100° C.; or between 70-100° C.; or between 80-100° C.; or between 90-100° C.; or between 75-100° C.

An illustrative example of the system comprising the UME cell is shown in FIG. 1. As illustrated in FIG. 1, the UME cell 101 contains a UME 102, a reference electrode 103, an optional salt bridge 104, an optional counter electrode 105, and an optional probe such as, but not limited to, temperature probe, pressure probe, pH probe, and/or TOC (Total Organic Carbon) meter 106. In some embodiments, all the components are fitted with compression fittings in the UME cell (not shown in the fig). The system further includes an optional adsorption unit 107 that may be operably connected to the UME cell 101. The flow of the aqueous medium (protocols described herein) in and out of the UME cell and/or through the adsorption unit may be controlled by a set of valves 108 which may be connected at various points through the system. The system may optionally be operably connected to a flush line to flush the cell with water or any other suitable solvent before and/or after the measurement of the metal ions. The system is also operably connected to the flow-in line of the aqueous medium comprising the metal ions and the one or more organic compounds. The system may optionally include a heating element 109 to keep the aqueous medium at a desired temperature. The system may optionally include a restricted orifice, pump, valve, or other device 110 to create pressure and force flow through UME assembly when valves are open. All the connections in the assembly could be flange, NPT, threaded, welded, and the like.

Based on the metal ion and the nature of the organic compound, the UME cell and its components may be chosen to prevent corrosion. For example, the UME cell may be made of Teflon, glass, PVC, or any other inert polymeric material.

In some embodiments of the systems, the systems further comprise a power source operably connected to the UME cell and configured to provide voltage/current to the cell.

It is to be understood that the components in the system illustrated in FIG. 1 may be arranged in a different order or arrangement depending on desired requirements. For example, more valves may be added or repositioned; the heating element may be repositioned, etc.

The systems provided herein can be used to carry out the methods described herein below. It is to be understood that one or more embodiments of the systems provided above may be combined in order to conduct the methods provided herein below.

Methods and Systems to Use UME

In order to avoid the deposition of the organic compound (s) on the surface of UME or to clean the surface of UME after deposition, and in order to measure the concentration of the metal ions effectively, Applicants found various methods and protocols to clean the surface of UME before, during, and/or after the measurement. Some embodiments of the methods are described herein below.

In one aspect, there is provided a method to measure concentration of metal ions with one or more organic compounds in an aqueous medium comprising:

contacting an aqueous medium comprising metal ions and one or more organic compounds with an ultramicroelectrode (UME) in a UME cell;

cleaning surface of the UME from deposition of the one or more organic compounds by passing a gas on the surface of UME, by forming a gas on the surface of UME, by mechanically cleaning the surface of UME, or combinations thereof;

subjecting the UME to a set Y of one or more potential cycles causing oxidation of the metal ions in the lower oxidation state to a higher oxidation state or causing reduction of the metal ions in higher oxidation state to a lower oxidation state; and measuring a steady state current thereby measuring the concentration of the metal ions.

In some embodiments of the foregoing aspect, the cleaning of the surface of the UME from the deposition of the one or more organic compounds by forming the gas on the surface of UME comprises subjecting the UME to a set X of one or more potential cycles to form oxygen gas, chlorine gas, hydrogen gas, sulfur dioxide gas, or combinations thereof, on the surface of the UME. In some embodiments, the voltage range of the set X of the one or more potential cycles is higher than reduction potential of the metal ion to prevent reduction of the metal and its deposition on the UME surface. In some embodiments, the voltage range of the set X of the one or more potential cycles is just below the open circuit potential of the metal ion, higher than the reduction potential of the metal ion, and/or higher than the potential at which gas is evolved at the UME such as chlorine gas, oxygen gas, hydrogen gas, etc. The range of the potential sweep at which gas is evolved at the UME can be broader or narrower as long as gas is evolved on the UME surface and the potential does not damage the UME or cause additional adsorption.

In some embodiments of the aspects and embodiments provided herein, the voltage range of the set X of the one or more potential cycles is between ±5V vs Standard Hydrogen Electrode (SHE), or between ±4V vs SHE, or between ±3V vs SHE, or between ±2V vs SHE, or between ±1V vs SHE, or between −1V to 2.5V vs SHE, or between −0.5V to 2.5V vs SHE, or between −0.6V to 2.5V vs SHE, or between OCP of the metal ions to 3V vs SHE, or between OCP of the metal ions to 2.5V vs SHE, or between OCP of the metal ions to 2V vs SHE, or between 0.2V to 2.5V vs SHE, or between 0.2V to 2V vs SHE, or between 0.2V to 1.5V vs SHE, or between 0.2V to 1V vs SHE, or between 0.2V to 0.5V vs SHE, or between 0.4V to 2.5V vs SHE, or between 0.4V to 2V vs SHE, or between 0.4V to 1.5V vs SHE, or 0.4V to 1V vs SHE, or between 0.6V to 2.5V vs SHE, or between 0.6V to 2V vs SHE, or between 0.6V to 1.5V vs SHE, or 0.6V to 1V vs SHE, or between 0.8V to 2.5V vs SHE, or between 0.8V to 2V vs SHE, or between 0.8V to 1.5V vs SHE, or between 1V to 2V vs SHE, or between 1V to 1.5V vs SHE. The SHE is only one type of reference electrode. Any number of reference electrodes known in the art can be used in the methods and systems of the invention for reference purposes. It is to be understood that the voltage for the metal ion may vary depending on the reference electrode being used with the UME.

The "potential cycles" as used herein, includes applying one or more fluctuating potentials to the electrode. For example, potential cycles include applying a potential (e.g. E1) to the electrode, ramping potential to a higher value to $E_{High}$ ($E_{High}$>E1), or to a lower value to $E_{low}$ ($E_{low}$<E1), then switching the direction of ramping to $E_{low}$ or $E_{High}$ for one or more cycles, and ending at a potential E2 (E2 can be equal to E1 or $E_{High}$ or $E_{low}$ or be a different potential)

The "reduction potential" as used herein, is a measure of the voltage at which there is a tendency of a chemical species such as metal ions, to acquire electrons and thereby be reduced. The reduction potential is measured in volts (V), or millivolts (mV).

The "oxidation potential" as used herein, is a measure of the voltage at which there is a tendency of a chemical species such as metal ions, to give electrons and thereby be oxidized. The oxidation potential is measured in volts (V), or millivolts (mV).

In some embodiments of the aspects and embodiments provided herein, the voltage range of the set Y of the one or more potential cycles comprises oxidation or reduction potential of the metal ion. In some embodiments, the voltage range of the set Y of the one or more potential cycles is between open circuit potential of the metal ion and oxidation potential or reduction potential of the metal ion depending on whether the metal is being oxidized or reduced for the measurement.

The "open circuit potential" or OCP, as used herein, is a potential measured in a solution of the metal ions when no current is passed through it. It is the potential where the system is at equilibrium. Different solutions have different open circuit potentials depending on the type of ions and concentration of ions. The OCP used in the methods and systems herein can be slightly higher or lower than the open circuit potential for a certain metal ion as long as this potential does not significantly alter the solution concentration near the UME surface.

In some embodiments, the voltage range of the set Y of the one or more potential cycles is between oxidation potential or reduction potential of the metal ion and any potential higher or lower than the oxidation or reduction potential of the metal ion. It is to be understood that the sweeping of the one or more potential cycles can be between any range of the potentials so long as the potential range includes the oxidation or reduction potential of the metal ion to cause oxidation of the metal ions in lower oxidation state to a higher oxidation state or cause reduction of the metal ions in higher oxidation state to a lower oxidation state. In some embodiments, the voltage range of the set Y of the one or more potential cycles comprises 0.65-0.85V vs SHE, or 0.65-1V vs SHE, or is between OCP of the metal ions and 0.85V vs SHE, or between OCP of the metal ions and 1V vs SHE, or between OCP of the metal ions and 0.3V above the OCP, or between OCP of the metal ions and 0.2V above the OCP, or between OCP of the metal ions and 0.1V above the OCP, or between OCP of the metal ions and 0.05V above the OCP. In some embodiments, the voltage range of the set Y of the one or more potential cycles comprises 0.65-0.85V vs SHE, or 0.65-1V vs SHE, or is between OCP of the metal ion and 0.85V vs SHE, or 1V vs SHE.

In some embodiments of the systems, the UME cell is configured to subject the UME to a set Y of one or more potential cycles causing oxidation of the metal ions in lower oxidation state to a higher oxidation state or causing reduction of the metal ions in higher oxidation state to a lower oxidation state. In some embodiments of the systems, the UME cell is configured to clean surface of the UME from deposition of the one or more organic compounds by forming a gas on the surface of UME. In some embodiments of the systems, the UME cell is configured to subject the UME to a set X of one or more potential cycles to form oxygen gas, chlorine gas, hydrogen gas, sulfur dioxide gas, or combinations thereof, on the surface of the UME. In some embodiments of the systems, the voltage range of the set Y of the one or more potential cycles comprises oxidation or reduction potential of the metal ion or is between open circuit potential of the metal ion and oxidation or reduction potential of the metal ion. In some embodiments of the systems, the voltage range of the set Y of the one or more potential cycles and the voltage range of the set X of one or more potential cycles, are as described above.

Accordingly, in some embodiments, there is provided a method to measure concentration of metal ions with one or more organic compounds in an aqueous medium comprising:

contacting an aqueous medium comprising metal ions and one or more organic compounds with an ultramicroelectrode (UME) in a UME cell;

cleaning surface of the UME from deposition of the one or more organic compounds by forming a gas on the surface of UME comprising subjecting the UME to a set X of one or more potential cycles to form oxygen gas, chlorine gas, hydrogen gas, sulfur dioxide gas, or combinations thereof, on the surface of the UME;

subjecting the UME to a set Y of one or more potential cycles causing oxidation of the metal ions in the lower oxidation state to a higher oxidation state or causing reduction of the metal ions in higher oxidation state to a lower oxidation state; and measuring a steady state current thereby measuring the concentration of the metal ions.

In some embodiments, there is provided a method to measure concentration of metal ions with one or more organic compounds in an aqueous medium comprising:

contacting an aqueous medium comprising metal ions and one or more organic compounds with an ultramicroelectrode (UME) in a UME cell;

cleaning surface of the UME from deposition of the one or more organic compounds by forming a gas on the surface of UME comprising subjecting the UME to a set X of one or more potential cycles to form oxygen gas, chlorine gas, hydrogen gas, sulfur dioxide gas, or combinations thereof, on the surface of the UME, wherein voltage range of the set X of the one or more potential cycles is just below the open circuit potential of the metal ion, higher than the reduction potential of the metal ion, and/or higher than the potential at which the gas is evolved at the UME;

subjecting the UME to a set Y of one or more potential cycles causing oxidation of the metal ions in the lower oxidation state to a higher oxidation state or causing reduction of the metal ions in higher oxidation state to a lower oxidation state, wherein voltage range of the set Y of the one or more potential cycles is between open circuit potential of the metal ion and oxidation potential or reduction potential of the metal ion; and measuring a steady state current thereby measuring the concentration of the metal ions.

In some embodiments, there is provided a method to measure concentration of metal ions with one or more organic compounds in an aqueous medium comprising:

contacting an aqueous medium comprising metal ions and one or more organic compounds with an ultramicroelectrode (UME) in a UME cell;

cleaning surface of the UME from deposition of the one or more organic compounds by forming a gas on the surface of UME comprising subjecting the UME to a set X of one or more potential cycles to form oxygen gas, chlorine gas, hydrogen gas, sulfur dioxide gas, or combinations thereof, on the surface of the UME, wherein voltage range of the set X of the one or more potential cycles is between ±5V vs Standard Hydrogen Electrode (SHE), or between ±4V vs SHE, or between ±3V vs SHE, or between ±2V vs SHE, or between ±1V vs SHE, or between −1V to 2.5V vs SHE, or between −0.5V to 2.5V vs SHE, or between −0.6V to 2.5V vs SHE, or between OCP of the metal ions to 3V vs SHE, or between OCP of the metal ions to 2.5V vs SHE, or between OCP of the metal ions to 2V vs SHE, or between 0.2V to 2.5V vs SHE, or between 0.2V to 2V vs SHE, or between 0.2V to 1.5V vs SHE, or between 0.2V to 1V vs SHE, or between 0.2V to 0.5V vs SHE, or between 0.4V to 2.5V vs SHE, or between 0.4V to 2V vs SHE, or between 0.4V to 1.5V vs SHE, or 0.4V to 1V vs SHE, or between 0.6V to 2.5V vs SHE, or between 0.6V to 2V vs SHE, or between 0.6V to 1.5V vs SHE, or 0.6V to 1V vs SHE, or between 0.8V to 2.5V vs SHE, or between 0.8V to 2V vs SHE, or between 0.8V to 1.5V vs SHE, or between 1V to 2V vs SHE, or between 1V to 1.5V vs SHE;

subjecting the UME to a set Y of one or more potential cycles causing oxidation of the metal ions in the lower oxidation state to a higher oxidation state or causing reduction of the metal ions in higher oxidation state to a lower oxidation state, wherein the voltage range of the set Y of the one or more potential cycles is between 0.65-0.85V vs SHE, or 0.65-1V vs SHE, or is between OCP of the metal ions and 0.85V vs SHE, or between OCP of the metal ions and 1V vs SHE, or between OCP of the metal ions and 0.3V above the OCP, or between OCP of the metal ions and 0.2V above the OCP, or between OCP of the metal ions and 0.1V above the OCP, or between OCP of the metal ions and 0.05V above the OCP; and measuring a steady state current thereby measuring the concentration of the metal ions.

In some embodiments, there is provided a method to measure concentration of copper ions with one or more organic compounds in an aqueous medium comprising:

contacting an aqueous medium comprising copper ions and one or more organic compounds with an ultramicroelectrode (UME) in a UME cell;

cleaning surface of the UME from deposition of the one or more organic compounds by forming a gas on the surface of UME comprising subjecting the UME to a set X of one or more potential cycles to form oxygen gas, chlorine gas, hydrogen gas, or combinations thereof, on the surface of the UME, wherein voltage range of the set X of the one or more potential cycles is between 0.2V to 2.5V vs SHE or between 0.4V to 2.5V vs SHE, or between 0.6V to 2.5V vs SHE;

subjecting the UME to a set Y of one or more potential cycles causing oxidation of the copper ions from Cu(I) to Cu(II) state, wherein voltage range of the set Y of the one or more potential cycles is between 0.65-0.85V vs SHE or between OCP and 0.85V vs SHE or 1V vs SHE; and measuring a steady state current thereby measuring the concentration of the copper ions.

Accordingly, in some embodiments, there are provided systems that carry out the foregoing methods.

In some embodiments, there is provided a system configured to measure concentration of metal ions in presence of one or more organic compounds in an aqueous medium comprising:

a UME cell comprising a UME configured to measure concentration of metal ions in an aqueous medium comprising one or more organic compounds; and the aqueous medium comprising metal ions and the one or more organic compounds, wherein the UME cell is configured to clean surface of the UME from deposition of the one or more organic compounds by forming a gas on the surface of UME by subjecting the UME to a set X of one or more potential cycles to form oxygen gas, chlorine gas, hydrogen gas, sulfur dioxide gas, or combinations thereof, on the surface of the UME;

wherein the UME cell is configured to subject the UME to a set Y of one or more potential cycles causing oxidation of the metal ions in lower oxidation state to a higher oxidation state or causing reduction of the metal ions in higher oxidation state to a lower oxidation state; and wherein the system is configured to measure steady state current from the UME, thereby measuring the concentration of the metal ions.

In some embodiments, there is provided a system configured to measure concentration of metal ions in presence of one or more organic compounds in an aqueous medium comprising:

a UME cell comprising a UME configured to measure concentration of metal ions in an aqueous medium comprising one or more organic compounds; and the aqueous medium comprising metal ions and the one or more organic compounds, wherein the UME cell is configured to clean surface of the UME from deposition of the one or more organic compounds by forming a gas on the surface of UME by subjecting the UME to a set X of one or more potential cycles just below the open circuit potential of the metal ion, higher than the reduction potential of the metal ion, and/or higher than the potential at which the gas is evolved at the UME to form oxygen gas, chlorine gas, hydrogen gas, sulfur dioxide gas, or combinations thereof, on the surface of the UME;

wherein the UME cell is configured to subject the UME to a set Y of one or more potential cycles between open circuit potential of the metal ion and oxidation potential or reduction potential of the metal ion causing oxidation of the metal ions in lower oxidation state to a higher oxidation state or causing reduction of the metal ions in higher oxidation state to a lower oxidation state; and wherein the system is configured to measure steady state current from the UME, thereby measuring the concentration of the metal ions.

In some embodiments, there is provided a system configured to measure concentration of metal ions in presence of one or more organic compounds in an aqueous medium comprising:

a UME cell comprising a UME configured to measure concentration of metal ions in an aqueous medium comprising one or more organic compounds; and the aqueous medium comprising metal ions and the one or more organic compounds, wherein the UME cell is configured to clean surface of the UME from deposition of the one or more organic compounds by forming a gas on the surface of UME by subjecting the UME to a set X of one or more potential cycles to form oxygen gas, chlorine gas, hydrogen gas, sulfur dioxide gas, or combinations thereof, on the surface of the UME, wherein voltage range of the set X of the one or more potential cycles is between ±5V vs Standard Hydrogen Electrode (SHE), or between ±3V vs SHE, or between 0.2V to 2.5V vs SHE, or between 0.2V to 2V vs SHE, or between 0.2V to 1.5V vs SHE, or between 0.2V to 1V vs SHE, or between 0.2V to 0.5V vs SHE, or between 0.4V to 2.5V vs SHE, or between 0.4V to 2V vs SHE, or between 0.4V to 1.5V vs SHE, or 0.4V to 1V vs SHE, or between 0.6V to 2.5V vs SHE, or between 0.6V to 2V vs SHE, or between 0.6V to 1.5V vs SHE, or 0.6V to 1V vs SHE, or between 0.8V to 2.5V vs SHE, or between 0.8V to 2V vs SHE, or between 0.8V to 1.5V vs SHE, or between 1V to 2V vs SHE, or between 1V to 1.5V vs SHE;

wherein the UME cell is configured to subject the UME to a set Y of one or more potential cycles causing oxidation of the metal ions in lower oxidation state to a higher oxidation state or causing reduction of the metal ions in higher oxidation state to a lower oxidation state, wherein the voltage range of the set Y of the one or more potential cycles is between 0.65-0.85V vs SHE, or 0.65-1V vs SHE, or is between OCP of the metal ions and 0.85V vs SHE, or between OCP of the metal ions and 1V vs SHE, or between OCP of the metal ions and 0.3V above the OCP, or between OCP of the metal ions and 0.2V above the OCP, or between OCP of the metal ions and 0.1V above the OCP, or between OCP of the metal ions and 0.05V above the OCP; and wherein the system is configured to measure steady state current from the UME, thereby measuring the concentration of the metal ions.

In some embodiments, there is provided a system configured to measure concentration of copper ions in presence of one or more organic compounds in an aqueous medium comprising:

a UME cell comprising a UME configured to measure concentration of copper ions in an aqueous medium comprising one or more organic compounds; and the aqueous medium comprising copper ions and the one or more organic compounds, wherein the UME cell is configured to clean surface of the UME from deposition of the one or more organic compounds by forming a gas on the surface of UME by subjecting the UME to a set X of one or more potential cycles to form oxygen gas, chlorine gas, hydrogen gas, or combinations thereof, on the surface of the UME, wherein voltage range of the set X of the one or more potential cycles is between 0.2V to 2.5V vs SHE, or between 0.4V to 2.5V vs SHE, or between 0.6V to 2.5V vs SHE;

wherein the UME cell is configured to subject the UME to a set Y of one or more potential cycles causing oxidation of the copper ions in lower oxidation state to a higher oxidation state or causing reduction of the copper ions in higher oxidation state to a lower oxidation state, wherein the voltage range of the set Y of the one or more potential cycles is between 0.65-0.85V vs SHE or between OCP and 0.85V vs SHE or 1V vs SHE; and wherein the system is configured to measure steady state current from the UME, thereby measuring the concentration of the copper ions.

In the foregoing aspects and embodiments, the potential cycles are applied by using a power source which may be operated manually or be automated to provide various potential cycles for operation of the UME cell.

The above described methods and systems may be used to measure the concentration of any metal ion.

Table 1 below illustrates some examples of the Standard Oxidation Potentials for some metals:

TABLE 1

Standard Oxidation Potentials

| Oxidation Half-Reactions | | | | EMF or E° |
|---|---|---|---|---|
| K | → | $K^+$ | + $e^-$ | 2.93 |
| Ca | → | $Ca^{2+}$ | + 2 $e^-$ | 2.87 |
| Na | → | $Na^+$ | + $e^-$ | 2.71 |
| Mg | → | $Mg^{2+}$ | + 2 $e^-$ | 2.37 |
| Al | → | $Al^{3+}$ | + 3 $e^-$ | 1.66 |
| $H_2 + 2\ OH^-$ | → | $2\ H_2O$ | + 2 $e^-$ | 0.83 |
| Zn | → | $Zn^{2+}$ | + 2 $e^-$ | 0.76 |
| Cr | → | $Cr^{3+}$ | + 3 $e^-$ | 0.74 |
| Fe | → | $Fe^{2+}$ | + 2 $e^-$ | 0.44 |
| Cd | → | $Cd^{2+}$ | + 2 $e^-$ | 0.40 |
| $Pb + SO_4^{2-}$ | → | $PbSO_4$ | + 2 $e^-$ | 0.36 |
| Ni | → | $Ni^{2+}$ | + 2 $e^-$ | 0.25 |
| Sn | → | $Sn^{2+}$ | + 2 $e^-$ | 0.14 |
| Pb | → | $Pb^{2+}$ | + 2 $e^-$ | 0.13 |
| $H_2$ | → | $2\ H^+$ | + 2 $e^-$ | 0.00 |
| $Sn^{2+}$ | → | $Sn^{4+}$ | + 2 $e^-$ | −0.15 |
| Cu | → | $Cu^{2+}$ | + 2 $e^-$ | −0.34 |
| $2\ I^-$ | → | $I_2$ | + 2 $e^-$ | −0.54 |
| $Fe^{2+}$ | → | $Fe^{3+}$ | + $e^-$ | −0.77 |
| Ag | → | $Ag^+$ | + $e^-$ | −0.80 |
| $Au + 4\ Cl^-$ | → | $AuCl_4^-$ | + 3 $e^-$ | −1.00 |
| $2\ Br^-$ | → | $Br_2$ | + 2 $e^-$ | −1.07 |
| $2\ H_2O$ | → | $O_2 + 4\ H^+$ | + 4 $e^-$ | −1.23 |
| $2\ Cl^-$ | → | $Cl_2$ | + 2 $e^-$ | −1.36 |
| Au | → | $Au^{3+}$ | + 3 $e^-$ | −1.50 |
| $2\ F^-$ | → | $F_2$ | + 2 $e^-$ | −2.87 |

Table 2 below illustrates some examples of the Standard Reduction Potentials for some metals:

TABLE 2

Standard Electrode Potentials

| Reduction Half-Reaction | Standard Potential E° (volts) |
|---|---|
| $Li^+(aq) + e^- \rightarrow Li(s)$ | −3.04 |
| $K^+(aq) + e^- \rightarrow K(s)$ | −2.92 |
| $Ca^{2+}(aq) + 2e^- \rightarrow Ca(s)$ | −2.76 |
| $Na^+(aq) + e^- \rightarrow Na(s)$ | −2.71 |
| $Mg^{2+}(aq) + 2e^- \rightarrow Mg(s)$ | −2.38 |
| $Al^{3+}(aq) + 3e^- \rightarrow Al(s)$ | −1.66 |
| $Zn^{2+}(aq) + 2e^- \rightarrow Zn(s)$ | −0.76 |
| $Cr^{3+}(aq) + 3e^- \rightarrow Cr(s)$ | −0.74 |
| $Fe^{2+}(aq) + 2e^- \rightarrow Fe(s)$ | −0.41 |
| $Cd^{2+}(aq) + 2e^- \rightarrow Cd(s)$ | −0.40 |
| $Ni^{2+}(aq) + 2e^- \rightarrow Ni(s)$ | −0.23 |
| $Sn^{2+}(aq) + 2e^- \rightarrow Sn(s)$ | −0.14 |
| $Pb^{2+}(aq) + 2e^- \rightarrow Pb(s)$ | −0.13 |
| $Fe^{3+}(aq) + 3e^- \rightarrow Fe(s)$ | −0.04 |
| $2H^+(aq) + 2e^- \rightarrow H_2(g)$ | 0.00 |
| $Sn^{4+}(aq) + 2e^- \rightarrow Sn^{2+}(aq)$ | 0.15 |
| $Cu^{2+}(aq) + e^- \rightarrow Cu^+(aq)$ | 0.16 |
| $AgCl(s) + e^- \rightarrow Ag(s) + Cl^-(aq)$ | 0.22 |
| $Cu^{2+}(aq) + 2e^- \rightarrow Cu(s)$ | 0.34 |
| $ClO_3^-(aq) + H_2O(l) + 2e^- \rightarrow ClO_2^-(aq) + 2OH^-(aq)$ | 0.35 |
| $IO^-(aq) + H_2O(l) + 2e^- \rightarrow I^-(aq) + 2OH^-(aq)$ | 0.49 |
| $Cu^+(aq) + e^- \rightarrow Cu(s)$ | 0.52 |
| $I_2(s) + 2e^- \rightarrow 2I^-(aq)$ | 0.54 |
| $ClO_2^-(aq) + H_2O(l) + 2e^- \rightarrow ClO^-(aq) + 2OH^-(aq)$ | 0.59 |
| $Fe^{3+}(aq) + e^- \rightarrow Fe^{2+}(aq)$ | 0.77 |
| $Hg_2^{2+}(aq) + 2e^- \rightarrow 2Hg(l)$ | 0.80 |
| $Ag^+(aq) + e^- \rightarrow Ag(s)$ | 0.80 |
| $Hg^{2+}(aq) + 2e^- \rightarrow Hg(l)$ | 0.85 |
| $ClO^-(aq) + H_2O(l) + 2e^- \rightarrow Cl^-(aq) + 2OH^-(aq)$ | 0.90 |
| $2Hg^{2+}(aq) + 2e^- \rightarrow Hg_2^{2+}(aq)$ | 0.90 |
| $NO_3^-(aq) + 4H^+(aq) + 3e^- \rightarrow NO(g) + 2H_2O(l)$ | 0.96 |
| $Br_2(l) + 2e^- \rightarrow 2Br^-(aq)$ | 1.07 |
| $O_2(g) + 4H^+(aq) + 4e^- \rightarrow 2H_2O(l)$ | 1.23 |
| $Cl_2(g) + 2e^- \rightarrow 2Cl^-(aq)$ | 1.36 |
| $Ce^{4+}(aq) + e^- \rightarrow Ce^{3+}(aq)$ | 1.44 |
| $MnO_4^-(aq) + 8H^+(aq) + 5e^- \rightarrow Mn^{2+}(aq) + 4H_2O(l)$ | 1.49 |
| $H_2O_2(aq) + 2H^+(aq) + 2e^- \rightarrow 2H_2O(l)$ | 1.78 |
| $Co^{3+}(aq) + e^- \rightarrow Co^{2+}(aq)$ | 1.82 |
| $S_2O_8^{2-}(aq) + 2e^- \rightarrow 2SO_4^{2-}(aq)$ | 2.01 |
| $O_3(g) + 2H^+(aq) + 2e^- \rightarrow O_2(g) + H_2O(l)$ | 2.07 |
| $F_2(g) + 2e^- \rightarrow 2F^-(aq)$ | 2.87 |

Any of the oxidation potential or the reduction potential listed in Tables 1 and 2 above may be considered in determining the voltage range of the potential cycles for the measurement of the concentration of a particular metal ion.

In some embodiments of the methods and systems provided herein, the metal ion is copper or the metal ion is the metal ion of the metal halide such as copper halide or copper chloride. In some embodiments, the one or more organic compounds comprise chloroethanol and/or EDC.

In some embodiments, the cleaning of the surface of the UME from the deposition of the one or more organic compounds by passing the gas on the surface of UME comprises bubbling a hydrogen gas, bubbling an oxygen gas, or bubbling a chlorine gas on the surface of UME. This method may be used in conjunction with the application of the potential cycles or alone.

In some embodiments, the cleaning of the surface of the UME from the deposition of the one or more organic compounds by mechanically cleaning the surface of UME comprises mechanically scrubbing the surface of the UME to remove the deposition. This method may be used in conjunction with the application of the potential cycles and/or the bubbling of the gas, or alone.

In some embodiments, the concentration of the one or more organic compounds in the aqueous medium is between about 0.5-5000 ppm or as described herein. In some embodiments, the one or more organic compounds are as described herein, e.g. ethylene dichloride, chloroethanol, monochloroacetaldehyde, dichloroacetaldehyde, trichloroacetaldehyde, or combinations thereof. In some embodiments, the aqueous medium comprises more than 5 wt % water or as described herein. In some embodiments, the UME is gold, platinum, titanium, carbon, conductive polymer, or iridium. In some embodiments, the metal ion is iron, copper, tin, chromium, or combination thereof. In some embodiments, the metal ion is copper. In some embodiments, the concentration of the metal ions in the lower oxidation state is more than 0.5M or a total metal ion concentration in the aqueous medium is more than 1M or is between 0.5-7M or is between 0.5-6.5M or as described herein.

In some embodiments, the method further comprises subjecting the aqueous medium comprising metal ions and the one or more organic compounds to adsorption over an adsorbent before the contacting step wherein the adsorbent substantially adsorbs the one or more organic compounds from the aqueous medium.

In some embodiments, the aqueous medium comprises less than about 5000 ppm of the one or more organic compounds after the adsorption or as described herein. In some embodiments, the adsorbent is activated charcoal, alumina, activated silica, polymer, or combination thereof. In some embodiments, the adsorbent is polystyrene. In some embodiments, the aqueous medium is flowed through the UME to cause removal of gas bubbles on UME surface. In some embodiments, the flowing of the aqueous medium keeps the temperature substantially constant during the measurement.

In some embodiments, the method further comprises keeping the UME cell at temperature of between 50-100° C. or as described herein.

In some embodiments, the measurement of the metal ion in the lower oxidation state or the higher oxidation state is dependent on the solubility of the metal ion in a particular oxidation state. For example, Cu(I) is partially soluble in high concentration. In such cases, it may be desirable to oxidize the copper ion from lower oxidation state to higher oxidation state in the UME cell instead of reducing the higher oxidation state to the lower oxidation state in order to prevent the crashing out of the Cu(I) salt in the aqueous medium.

In some embodiments, the method further comprises subjecting the aqueous medium comprising Cu(I) ions and one or more organic compounds to adsorption over an adsorbent before contacting the aqueous medium with the UME to adsorb partially or substantially the one or more organic compounds over the adsorbent.

In some embodiments of the systems, the system is fully or partially automated through a control station. In some embodiments of the systems, the power source is automated to provide various potential cycles for operation of the UME cell in accordance with the methods provided herein.

In some embodiments, the systems of the invention may include a control station configured to control the amount of the aqueous medium introduced into the UME cell, the flow of the aqueous medium introduced into the UME cell, the flow of the flush line, voltage range of the one of more potential cycles from the power source applied to the UME (described herein), the adsorption time over the adsorbents, the temperature, pressure, pH, and/or TOC probes in the UME cell, the flow rate in and out of the UME cell, the closing and opening of the valves, etc. The control station may be connected to a computer and/or a PLC (pressure liquid chromatography) unit.

The control station may include a set of valves or multi-valve systems which are manually, mechanically or digitally controlled, or may employ any other convenient flow regulator protocol. In some instances, the control station may include a computer interface, (where regulation is computer-assisted or is entirely controlled by computer) configured to provide a user with input and output parameters to control the amount and conditions, as described above.

The methods and systems of the invention may also include one or more detectors configured for monitoring the flow of the aqueous medium or the concentration of the organics in the aqueous medium, etc. Monitoring may include, but is not limited to, collecting data about the pressure, temperature and composition of the aqueous medium and gases.

The detectors or probes described herein may be any convenient device configured to monitor, for example, pressure probes (e.g., electromagnetic pressure sensors, potentiometric pressure sensors, etc.), temperature probes (resistance temperature detectors, thermocouples, gas thermometers, thermistors, pyrometers, infrared radiation sensors, etc.), volume probes (e.g., geophysical diffraction tomography, X-ray tomography, hydroacoustic surveyers, etc.), and devices for determining chemical makeup of the aqueous medium or the gas (e.g, IR spectrometer, NMR spectrometer, UV-vis spectrophotometer, high performance liquid chromatographs, inductively coupled plasma emission spectrometers, inductively coupled plasma mass spectrometers, ion chromatographs, X-ray diffractometers, gas chromatographs, gas chromatography-mass spectrometers, flow-injection analysis, scintillation counters, acidimetric titration, and flame emission spectrometers, etc.).

In some embodiments, detectors may also include a computer interface which is configured to provide a user with the collected data about the aqueous medium, metal ions and/or the organics. For example, a detector may determine the concentration of the aqueous medium, metal ions and/or the organics and the computer interface may provide a summary of the changes in the composition within the aqueous medium, metal ions and/or the organics over time. In some embodiments, the summary may be stored as a computer readable data file or may be printed out as a user readable document.

In some embodiments, the detector may be a monitoring device such that it can collect real-time data (e.g., internal pressure, temperature, etc.) about the aqueous medium, metal ions and/or the organics. In other embodiments, the detector may be one or more detectors configured to determine the parameters of the aqueous medium, metal ions and/or the organics at regular intervals, e.g., determining the composition every 1 minute, every 5 minutes, every 10 minutes, every 30 minutes, every 60 minutes, every 100 minutes, every 200 minutes, every 500 minutes, or some other interval.

UME Methods and Systems Used in-Line with Other Methods and Systems

In the foregoing aspects and embodiments, the system comprising the UME cell and its components may be operably connected to any system that uses metal ions in any organic process, such as, but not limited to, organometallics, metallurgy, electrochemical and reactor systems provided herein, and the like. The system comprising the UME cell and its components may be connected in-line in any of these systems to measure the concentration of the metal ions in the presence of organics. Such measurement can help facilitate the operation of the processes.

In some embodiments, the UME system is operably connected to an electrochemical system and/or a reactor system described herein below. This connection of the UME cell with the reactor and the electrochemical system is illustrated in FIG. 2.

The electrochemical system and the reactor system, operably connected to the UME system provided herein, have been described in detail in US Patent Application Publication No. 2012/0292196, filed May 17, 2012; US Patent Application Publication No. 2013/0206606, filed Mar. 13, 2013; and US Patent Application Publication No. 2015/0038750, filed Jul. 30, 2014, all of which are incorporated herein by reference in their entireties.

Figure 2:
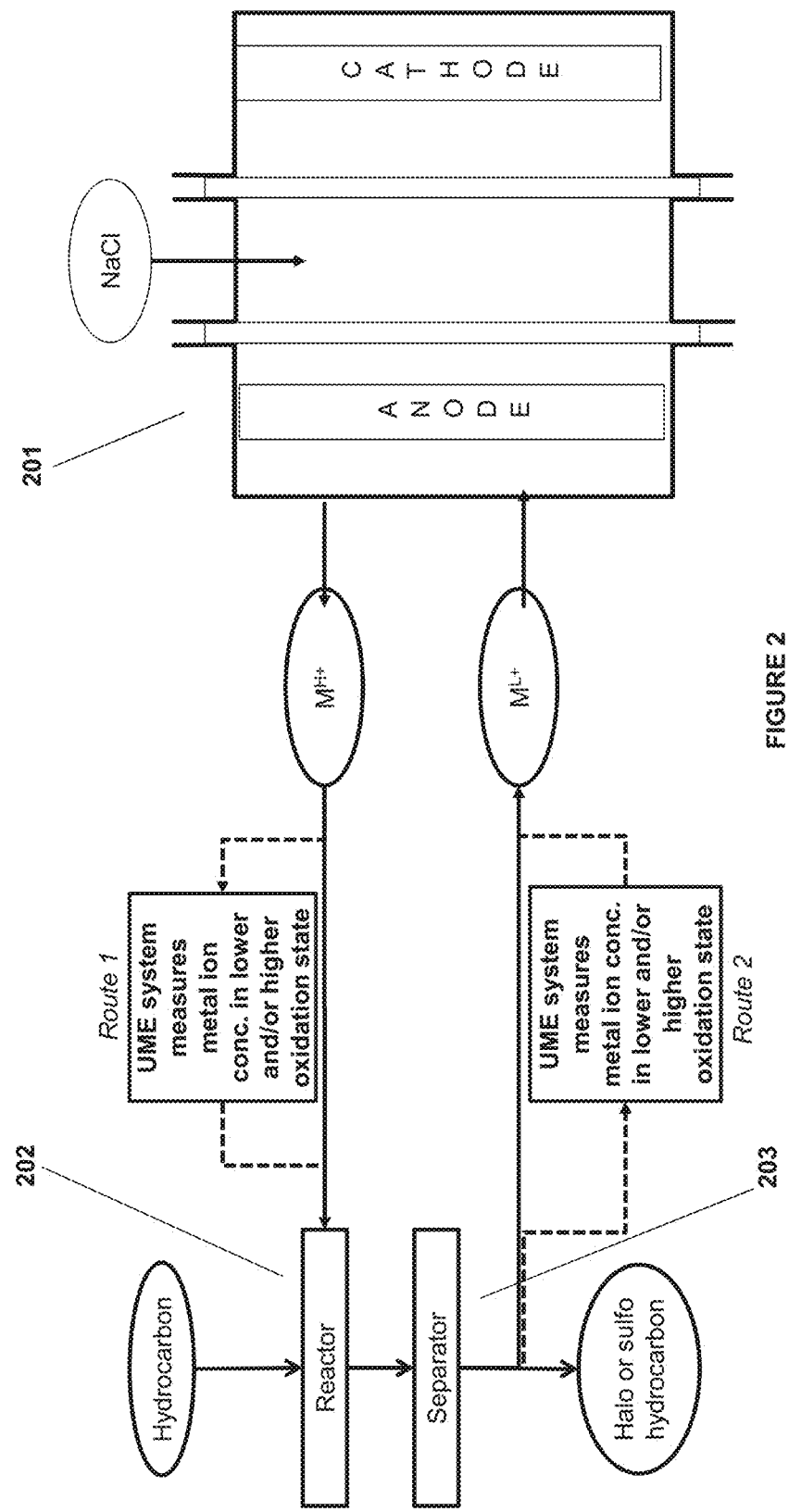
FIG. 2 is an illustration of some embodiments provided herein.

As illustrated in FIG. 2, the electrochemical cell 201 provided herein may be any electrochemical cell where the metal ion in the lower oxidation state is converted to the metal ion in the higher oxidation state in the anode chamber. In such electrochemical cells, cathode reaction may be any reaction that does or does not form an alkali in the cathode chamber. Such cathode consumes electrons and carries out any reaction including, but not limited to, the reaction of water to form hydroxide ions and hydrogen gas; or reaction of oxygen gas and water to form hydroxide ions; or reduction of protons from an acid such as hydrochloric acid to form hydrogen gas; or reaction of protons from hydrochloric acid and oxygen gas to form water. In some embodiments, the electrochemical cells may include production of alkali in the cathode chamber of the cell.

The electrochemical system includes an anode and a cathode separated by ion exchange membranes such as anion exchange membrane (AEM) and/or a cation exchange membrane (CEM) creating a third chamber containing a third electrolyte, e.g. NaCl. The anode chamber includes the anode and an anode electrolyte in contact with the anode. The cathode chamber includes the cathode and a cathode electrolyte in contact with the cathode. The metal ion is oxidized in the anode chamber from the lower oxidation state $M^{L+}$ to the higher oxidation state $M^{H+}$ which metal in the higher oxidation state is then used for reactions in a reactor 202. The reaction of the metal ion in the higher oxidation state with hydrocarbon, such as, unsaturated or saturated hydrocarbon in the reactor 202 produces one or more organic compounds such as halohydrocarbon or sulfohydrocarbon. The metal ion in the higher oxidation state is consequently reduced to metal ion in the lower oxidation state in the reactor. The metal ion solution is separated from the halohydrocarbon or sulfohydrocarbon (organics) in a separator 203 before the metal ion solution is recirculated back to the anode electrolyte of the electrochemical system. While the electrochemical cell illustrated in FIG. 2 has both the AEM and CEM, the electrochemical cell may not comprise a third chamber and may have only one ion exchange membrane (AEM or CEM).

The "reactor" as used herein is any vessel or unit in which the organic reaction, such as, but not limited to, halogenation or sulfonation reaction is carried out. The reactor is configured to contact the metal ion in the higher oxidation state, such as, e.g. only metal chloride or metal sulfate, from the anode electrolyte of the electrochemical cell with the unsaturated or saturated hydrocarbon. The reactor may be any means for contacting the metal halide or metal sulfate in the anode electrolyte with the unsaturated or saturated hydrocarbon. Such means or such reactor are well known in the art and include, but not limited to, pipe, column, duct, tank, series of tanks, container, tower, conduit, and the like.

The "halohydrocarbon" or "halogenated hydrocarbon" as used herein, includes halo substituted hydrocarbons where halo may be any number of halogens that can be attached to the hydrocarbon based on permissible valency. The halogens include fluoro, chloro, bromo, and iodo. The examples of halohydrocarbons include chlorohydrocarbons, bromohydrocarbons, and iodohydrocarbons. The chlorohydrocarbons include, but not limited to, monochlorohydrocarbons, dichlorohydrocarbons, trichlorohydrocarbons, etc. For metal halides, such as, but not limited to, the metal chloride, metal bromide or metal iodide with the higher oxidation state produced by the anode chamber can be used for purposes, such as, but not limited to, generation of chloro, bromo or iodohydrocarbons, such as, but not limited to, monochlorohydrocarbons, dichlorohydrocarbons, trichlorohydrocarbons, monobromohydrocarbons, dibromohydrocarbons, tribromohydrocarbons, monoiodohydrocarbons, diiodohydrocarbons, triiodohydrocarbons, etc (also called one or more organic compounds). The hydrocarbon in the halo or sulfo hydrocarbon is any hydrocarbon from which the halo or sulfo hydrocarbon is generated. For example, EDC is the halogenated hydrocarbon generated from ethylene by addition of chlorine atoms on the double bond or EDC is the halogenated hydrocarbon generated from ethane by replacement of the hydrogens by the chlorine atoms. These halohydrocarbon or halogenated hydrocarbons are examples of the one or more organic compounds that may be present in the aqueous medium that is tested for metal ion concentration in the UME systems provided herein.

The "sulfohydrocarbons" as used herein include hydrocarbons substituted with one or more of —$SO_3H$ or —$OSO_2OH$ based on permissible valency. These sulfohydrocarbons are examples of the one or more organic compounds that may be present in the aqueous medium that is tested for metal ion concentration in the UME systems provided herein.

The "unsaturated hydrocarbon" as used herein, includes a hydrocarbon with unsaturated carbon or hydrocarbon with at least one double and/or at least one triple bond between adjacent carbon atoms. The unsaturated hydrocarbon may be linear, branched, or cyclic (aromatic or non-aromatic). For example, the hydrocarbon may be olefinic, acetylenic, non-aromatic such as cyclohexene, aromatic group or a substituted unsaturated hydrocarbon such as, but not limited to, halogenated unsaturated hydrocarbon. The hydrocarbons with at least one double bond may be called olefins or alkenes and may have a general formula of an unsubstituted alkene as $C_nH_{2n}$ where n is 2-20 or 2-10 or 2-8, or 2-5. In some embodiments, one or more hydrogens on the alkene may be further substituted with other functional groups such as but not limited to, halogen (including chloro, bromo, iodo, and fluoro), carboxylic acid (—COOH), hydroxyl (—OH), amines, etc. The unsaturated hydrocarbons include all the isomeric forms of unsaturation, such as, but not limited to, cis and trans isomers, E and Z isomers, positional isomers etc.

Examples of substituted or unsubstituted alkenes include, but not limited to, ethylene, chloro ethylene, bromo ethylene, iodo ethylene, propylene, chloro propylene, hydroxyl propylene, 1-butylene, 2-butylene (cis or trans), isobutylene, 1,3-butadiene, pentylene, hexene, cyclopropylene, cyclobutylene, cyclohexene, etc.

The hydrocarbons with at least one triple bond maybe called alkynes and may have a general formula of an unsubstituted alkyne as $C_nH_{2n-2}$ where n is 2-10 or 2-8, or 2-5. In some embodiments, one or more hydrogens on the alkyne may be further substituted with other functional groups such as but not limited to, halogen, carboxylic acid, hydroxyl, etc. Examples of substituted or unsubstituted alkynes include, but not limited to, acetylene, propyne, chloro propyne, bromo propyne, butyne, pentyne, hexyne, etc.

In some embodiments, the unsaturated hydrocarbon reacted in the reactor, as described herein, is C2-C10 alkene or C2-C8 alkene or C2-C6 alkene or C2-C5 alkene or C2-C4 alkene or C2-C3 alkene. In some embodiments, the unsaturated hydrocarbon is C2-C10 alkyne or C2-C8 alkyne or C2-C6 alkyne or C2-C5 alkyne or C2-C4 alkyne or C2-C3 alkyne. In some embodiments of the methods and systems described herein, the unsaturated hydrocarbon described herein is, ethylene. The halohydrocarbon are one or more of the organic compounds formed from such unsaturated hydrocarbon is e.g., ethylene dichloride (EDC), chloroethanol, butyl chloride, dichlorobutane, chlorobutanol, etc.

The "saturated hydrocarbon" as used herein, includes a hydrocarbon with no unsaturated carbon or hydrocarbon. The hydrocarbon may be linear, branched, or cyclic. For example, the hydrocarbon may be substituted or unsubstituted alkanes and/or substituted or unsubstituted cycloalkanes. The hydrocarbons may have a general formula of an unsubstituted alkane as $C_nH_{2n+2}$ where n is 2-20 or 2-10 or 2-8, or 2-5. In some embodiments, one or more hydrogens on the alkane or the cycloalkanes may be further substituted with other functional groups such as but not limited to, halogen (including chloro, bromo, iodo, and fluoro), carboxylic acid (—COOH), hydroxyl (—OH), amines, etc.

Examples of substituted or unsubstituted alkanes $C_nH_{2n+2}$ where n is 2-20 or 2-10 or 2-8, or 2-6 or 2-5 include, but not limited to, methane, ethane, chloroethane, bromoethane, iodoethane, propane, chloropropane, hydroxypropane, butane, chlorobutane, hydroxybutane, pentane, hexane, cyclohexane, cyclopentane, chlorocyclopentane, octane, decane, etc.

The above recited unsaturated or saturated hydrocarbons may be treated with metal salts with metal ion in the higher oxidation state to form one or more organic compounds such as, halohydrocarbons or sulfohydrocarbons and the metal ions in the lower oxidation state in the aqueous medium. It is to be understood that the aqueous medium may contain a mixture of both the metal ions in the lower oxidation state as well as the metal ions in the higher oxidation state. Such aqueous medium with organics and metal ions is then tested for the concentration of the metal ion (in lower or higher oxidation state) in the UME systems described herein.

In some embodiments, the UME system of the invention may be connected in line between the reactor system and the electrochemical system such that the anode electrolyte (or the aqueous medium) coming out of the electrochemical system (illustrated as route 1 in FIG. 2) and going to the reactor and/or the aqueous medium coming out of the reactor/separator and going into the electrochemical system (illustrated as route 2 in FIG. 2) may be tested for measuring the metal ion concentration for the metal ion in the lower or the higher oxidation state. In some embodiments, the UME system of the invention may also be connected to the electrochemical system to measure the concentration of the metal ion going into the anode chamber and coming out of the anode chamber of the electrochemical cell. In some embodiments, the UME system of the invention may also be connected to the reactor to measure the concentration of the metal ion going into the reactor and coming out of the reactor.

The metal ion solution going into the anode electrolyte and the metal ion solution coming out of the anode electrolyte may contain a mix of the metal ion in the lower oxidation state and the higher oxidation state except that the metal ion solution coming out of the anode has higher amount of metal ion in the higher oxidation state than the metal ion solution going into the anode electrolyte. Similarly, the metal ion solution going into the reactor and the metal ion solution coming out of the reactor may contain a mix of the metal ion in the lower oxidation state and the higher oxidation state except that the metal ion solution coming out of the reactor has higher amount of metal ion in the lower oxidation state than the metal ion solution going into the reactor.

In some embodiments, the in-line measurement of the metal ion concentration such as in the systems of the invention facilitates optimization of the concentration of the metal ion in the lower oxidation state or the higher oxidation state in the aqueous medium before, during, and/or after its administration to the anode chamber of the electrochemical cell and/or the reactor. This in some embodiments may facilitate optimized operation of the electrochemical system as well as the reactor. The measurement and the optimization of the metal ion in the lower oxidation state and the higher oxidation state and their ratios may assist in achieving lower voltages in the electrochemical systems and high yield and selectivity in corresponding catalytic reactions with hydrocarbons in the reactor systems. Therefore, it may be desirable to measure the concentration of the metal ion in the lower oxidation state and/or the higher oxidation state using the UME systems of the invention in order to optimize the ratio of the metal ions in the lower oxidation states and the higher oxidation state in the aqueous medium.

Accordingly, in some embodiments the methods provided herein further comprise, obtaining the aqueous medium (before the contacting step) from a reactor after a reaction in the reactor of an unsaturated or saturated hydrocarbon with the metal ion in the higher oxidation state in an aqueous medium, to form one or more organic compounds and the metal ion in the lower oxidation state in the aqueous medium. In some embodiments of the foregoing embodiment, the method further comprises obtaining the aqueous medium comprising the metal ion in the higher oxidation state after oxidizing the metal ion from a lower oxidation state to a higher oxidation state in the anode electrolyte at an anode of an electrochemical cell.

In some embodiments, the measurement of the concentration of the metal ion in the lower or the higher oxidation state in the aqueous medium is conducted before, during, and/or after administration of the aqueous medium to an anode chamber of an electrochemical cell where the metal ion is oxidized from the lower oxidation state to the higher oxidation state at an anode. In some embodiments, the measurement of the concentration of the metal ion in the lower or the higher oxidation state in the aqueous medium facilitates optimization of the concentration of the metal ion in the aqueous medium before, during, and/or after its administration to the anode chamber of the electrochemical cell.

In some embodiments, the measurement of the concentration of the metal ion in the lower or the higher oxidation state in the aqueous medium is conducted before, during, and/or after administration of the aqueous medium to a reactor where the metal ion in the higher oxidation state in the aqueous medium is reacted with an unsaturated or saturated hydrocarbon to form one or more organic compounds and the metal ion in the lower oxidation state in the aqueous medium. In some embodiments, the aqueous medium comprises a mixture of metal ions in lower and higher oxidation state.

In the foregoing aspects and embodiments, the system comprising UME cell and its components may be operably connected to the reactor such that the aqueous medium comprising metal ions in lower oxidation state and one or more organic compounds is then transferred to the UME cell for the measurement of the concentration of the metal ions in the lower or the higher oxidation state. In some embodiments, the reactor may be operably connected to the adsorption unit which in turn is connected to the UME cell. The systems may be operably connected to each other through pipes, tubes, conduits, tanks, and the like.

In such reactor and electrochemical systems where the metal ions are constantly reduced and oxidized, respectively, the measurement of the metal ion concentration in the lower and/or the higher oxidation state can help facilitate smooth and efficient functioning of the reactor as well as the electrochemical systems.

In some embodiments, the ratio of the metal ion in the higher oxidation state to the metal ion in the lower oxidation state in the aqueous medium that is tested using the UME of the invention, is between 20:1 to 1:20, or between 14:1 to 1:2; or between 14:1 to 8:1; or between 14:1 to 7:1: or between 2:1 to 1:2; or between 1:1 to 1:2; or between 4:1 to 1:2; or between 7:1 to 1:2.

In some embodiments of the methods and systems described herein, the anode electrolyte in the electrochemical systems operably connected to the UME systems contains the metal ion in the higher oxidation state in the range of 4-7M, and the metal ion in the lower oxidation state in the range of 0.1-2M. In some embodiments of the methods and systems described herein, the anode electrolyte reacted with the unsaturated or saturated hydrocarbon in the reactor contains the metal ion in the higher oxidation state in the range of 4-7M, and the metal ion in the lower oxidation state in the range of 0.1-2M. The anode electrolyte may optionally contain 0.01-0.1 M hydrochloric acid.

In some embodiments, the anode electrolyte may contain metal ion in the lower oxidation state and negligible or low amounts of the metal ion in the higher oxidation state for higher voltage efficiencies. The metal ion in the higher oxidation state may be supplemented to the exiting metal solution from the electrochemical cell before being fed into the reactor for the reaction with the hydrocarbon. Before the metal ion solution is circulated back to the electrochemical cell from the reactor, the metal ion in the higher oxidation state may be removed or separated and the solution predominantly containing the metal ion in the lower oxidation state may be fed to the electrochemical cell after testing in the UME systems of the invention.

In some embodiments of the methods and systems described herein, the amount of the metal ion in the aqueous medium that is tested using the UME systems of the invention, is between 0.5-8M; or between 0.5-7M; or between 0.5-6M; or between 0.5-5M; or between 0.5-4M; or between 0.5-3M; or between 0.5-2M; or between 0.5-1M; or between 1-8M; or between 1-7M; or between 1-6M; or between 1-5M; or between 1-4M; or between 1-3M; or between 1-2M; or between 2-8M; or between 2-7M; or between 2-6M; or between 2-5M; or between 2-4M; or between 2-3M; or between 3-8M; or between 3-7M; or between 3-6M; or between 3-5M; or between 3-4M; or between 4-8M; or between 4-7M; or between 4-6M; or between 4-5M; or between 5-8M; or between 5-7M; or between 5-6.5M; or between 5-6M; or between 6-8M; or between 6-7M; or between 7-8M. In some embodiments, the amount of the total ion in the aqueous medium, as described above, is the amount of the metal ion in the lower oxidation state plus the amount of the metal ion in the higher oxidation state; or the total amount of the metal ion in the higher oxidation state; or the total amount of the metal ion in the lower oxidation state.

It is to be understood that the system 201 of FIG. 2 is for illustration purposes only and metal ions with different oxidations states (e.g., chromium, tin etc.); other electrochemical systems; the third electrolyte other than sodium chloride such as sodium sulfate or HCl; and cathodes producing hydroxide, water and/or hydrogen gas, are variations that are equally applicable to this system. It is also to be understood that the reactor 202 may be a combination of one or more reactors and the separator 203 may be a combination of one or more separators or separation units.

Kit

In yet another aspect, there is provided a kit comprising: a UME cell comprising a UME configured to measure concentration of metal ions in an aqueous medium comprising one or more organic compounds. In some embodiments, the UME cell further comprises a reference electrode and optionally a working electrode. In some embodiments, the UME cell further comprises tubes, valves, pH probe, temperature probe, pressure probe, TOC meter, or combinations thereof. In some embodiments, the UME cell further comprises compression fittings to withstand high pressurized liquid through the UME cell. In some embodiments, the kit comprises all the components that have been described herein related to UME systems. In some embodiments, the kit further comprises an instruction manual that provides instructions or protocol on how to use the UME cell. In some embodiments, the kit further comprises a CD, disk, or USB comprising a computer software program to operate the UME cell. In some embodiments, the kit further comprises an adsorption unit to be operably connected to the UME cell comprising an adsorbent configured to adsorb the one or more organic compounds from the aqueous medium. The adsorption unit and the adsorbent have been described herein.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Various modifications of the invention in addition to those described herein will become apparent to those skilled in the art from the foregoing description and accompanying figures. Such modifications fall within the scope of the appended claims. Efforts have been made to ensure accuracy with respect to numbers used (e.g. amounts, temperature, etc.) but some experimental errors and deviations should be accounted for.

EXAMPLES

Example 1

Application of Two Sets of Potential Cycles for Measurement of Metal Ion Concentration in the Presence of Organics In this experiment, a three electrodes system was used, containing 25 μm platinum microelectrode (e.g. from CH Instruments), Ag|AgCl reference electrode and salt bridge (e.g. from Gamry), and a platinum wire. The bottom half of the UME cell was immersed in water bath where the temperature was around 90° C. The copper flow was controlled by a peristaltic pump. In some experiments, the flow through the UME cell was controlled by opening and closing the valves on either side of the UME cell.

For the first set of potential cycles, the potential applied on the electrode was swept from 0.45V to 2V at 0.5V/s for 10 cycles. The potential window was dictated by the Cu(I)Cl reduction potential and $O_2/Cl_2$ evolution potential. Below 0.45V, the Cu(I) could be reduced to metallic copper and deposited on the UME surface, which was avoided. At around 1.5V, the UME started to evolve gas, but only after ~1.7V to 1.8V, it evolved more gas (for the complete cleaning of the UME surface). Above 2V, the current for gas evolution increased to more than 1000 μA, which may be damaging over the long-term. So the desired potential window for copper ion may be higher than 1.5V but not much higher than 2V. The number of cycles was determined by the current during the gas evolution. Usually after 3~5 cycles, the current response became reproducible, indicating the surface of the electrode had reached a stable/clean state. The scan rate was limited by the potentiostat. Under the current measurement mode, the max scan rate was 0.5V/s. With different mode/potentiostat, the scan rate could be a few volts per second. The copper solution was kept as flowing during gas evolution for two reasons: to minimize the temperature drop and chances of copper solution crush out; and to sweep away the gas bubbles so they won't block the UME surface.

After the cleaning step, the flow was stopped after ~10 s to allow fresh solution going into the cell as well as sweep away the gas bubbles. The measurements were taken 10 s after the flow stopped, to allow the solution to be fully stagnant. Data showed that the measurements were stable several minutes after the cleaning, which suggested that the measurement did not have to be taken right away as long as the solution could be kept at constant temperature. During measurements, a series of potential steps were applied: first at open circuit potential, then at 0.65V vs Ag|AgCl reference electrode, then open circuit potential again, and 0.65V again. There were total of 12 steps and 6 for each potential. Every step lasted 2 s. The sampling rate was at 0.002 s. The curves were then fitted to extrapolate diffusion coefficient, and then to calculate normalized steady state current which represented Cu(I) concentration.

Example 2

Figure 3:
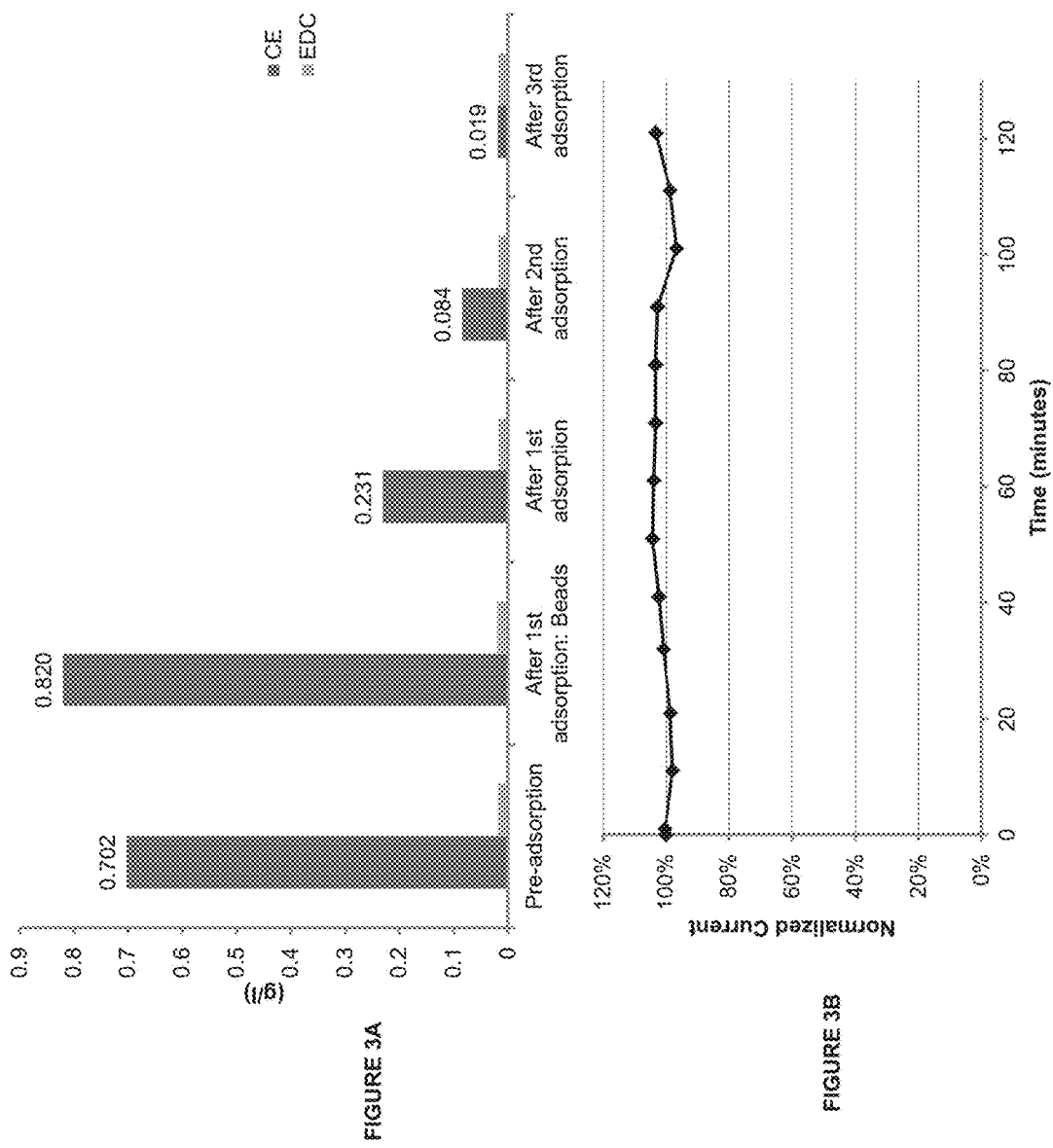
FIG. 3A is an illustration of some embodiments provided in Example 2 herein.
FIG. 3B is an illustration of some embodiments provided in Example 2 herein.

Application of Potential Cycles for Measurement of Metal Ion Concentration in the Presence of Organics Pre-Adsorption Using Polystyrene Beads:

In the lab setup, 100 g of polystyrene beads were added to 500 ml of copper solution (5M $CuCl_2$, 1M CuCl and 2.5M NaCl) containing 500~1000 ppm of chlorethanol (CE). After 15 minutes, the beads were filtered out, and fresh beads (100 g) were added into the solution. After 3 times, the CE level in the solution was reduced to 20 ppm or less (as measured by gas chromatography), as illustrated in FIG. 3A. The copper solution was then run through UME cell, and the copper(I) concentration (as current measured) was found to be stable as illustrated in FIG. 3B, compared to the constant decay without polystyrene beads adsorption.

Figure 4:
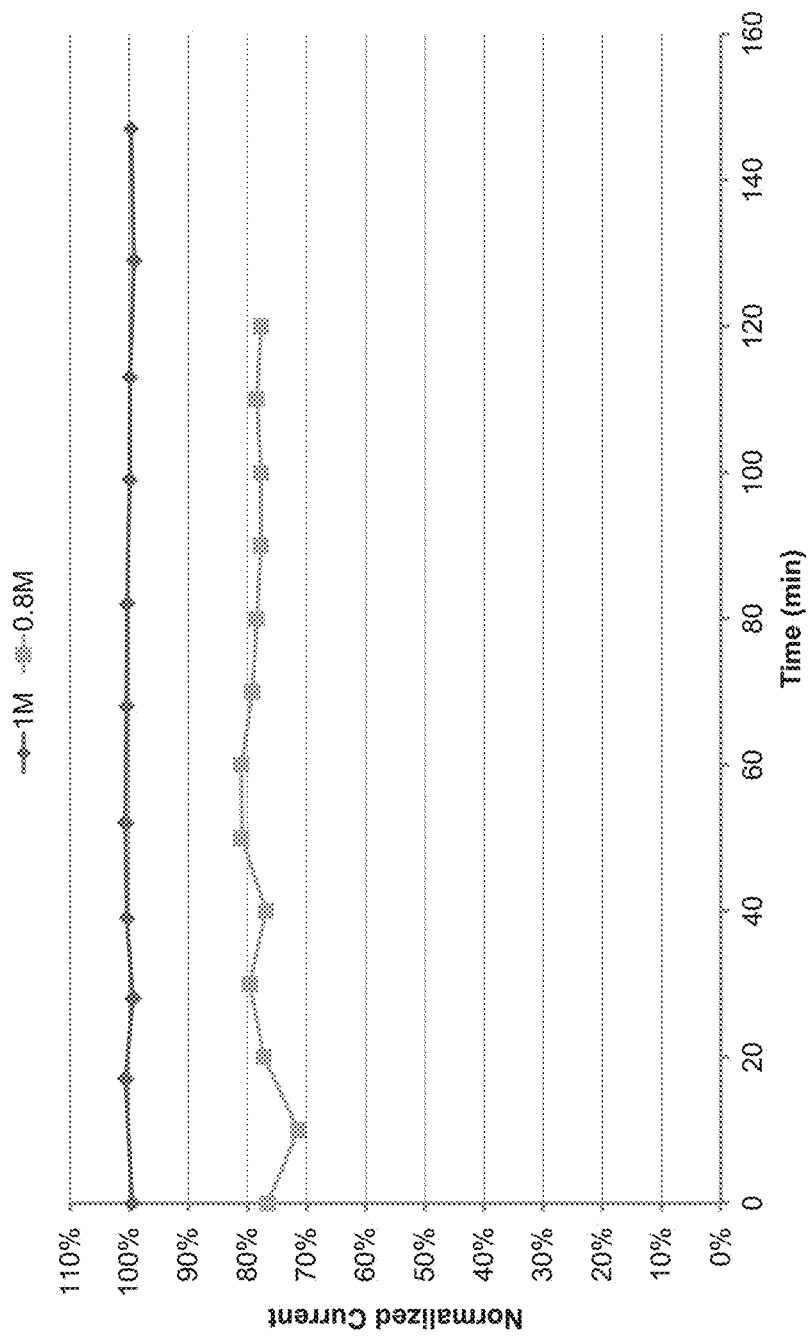
FIG. 4 is an illustration of some embodiments provided in Example 2 herein.

Electrode Surface Treatment by as Evolution:

In the lab setup, copper solution (4.5M $CuCl_2$, 1M or 0.8M CuCl and 2.5M NaCl) containing 500~1000 ppm of CE was allowed to flow through the UME cell at around 300 l/h. During flow condition, the UME was swept between 0.45V and 2V for 10 cycles. At high voltage, oxygen and chlorine gas were evolved on the surface of the electrode, thus cleaning the surface. After the cleaning steps, the flow was stopped, and the current measurements were taken. The tests results showed stable current with this method, as illustrated in FIG. 4. The current was found to be stable for 2 hrs after the gas evolution as compared to decay within an hour when no gas cleaning was done.

Example 3

Measurement of Metal Ion Concentration in the Presence of Organics with and without Cleaning Steps In this experiment, a three electrodes system was used, containing 25 μm platinum microelectrode (e.g. from CH Instruments), Ag|AgCl reference electrode and salt bridge (e.g. from Gamry), and a platinum wire. The bottom half of the UME cell was immersed in water bath where the temperature was around 90° C. or was controlled around 90° C. by heat stripes and insulation (measured by a thermocouple). The copper flow was controlled by a peristaltic pump or by a diaphragm valve and two solenoid valves. In some experiments, the flow through the UME cell was controlled by opening and closing the valves on either side of the UME cell. Table I below represents experiments for the measurement of the metal ion concentration using UME without the cleaning steps and Table II below represents experiments for the measurement of the metal ion concentration using UME with the cleaning steps.

TABLE I

UME organic fouling without cleaning steps

| No. | $CuCl_2$/ CuCl/ NaCl (M) | Organics | Duration | Result (current) |
|---|---|---|---|---|
| 1 | 5/1/2.5 | 600 ppm CE | 90 min | Initial 100%, raised to 104% then dropped to 96% by the end of experiment |
| 2 | 5/1/2.5 | 600 ppm CE pre-soaked for 24 h | 3 h | Initial 100%, dropped to 94% by the end of experiment |
| 3 | 4.5-5.5/ 0.8-1.2/ 2.2-2.5 | Mixture of organics >500 ppm | 50 h | Initial 100%, dropped to 57% by the end of experiment |

TABLE II

UME stability with cleaning steps

| No. | $CuCl_2$/ CuCl/ NaCl (M) | Organics | Duration | Result |
|---|---|---|---|---|
| 4 | 4.5/1/2.5 | 600 ppm | 2.5 h | Initial 100%, stable between 100% to 101% during whole experiment |
| 5 | 4.5/0.8/2.5 | 600 ppm | 2 h | Initial 100%, stable between 98% to 104% during whole experiment |
| 6 | 4.5/1/2.5 | 600 ppm | 2.5 h | Initial 100%, stable between 99% to 101% during whole experiment |
| 7 | constant within 4.5~5.5/ 0.8~1.2/ | Mixture of organics >500 ppm | 10 h | Initial 100%, stable between 98% to 102% during whole experiment |

TABLE II-continued

UME stability with cleaning steps

| No. | CuCl$_2$/ CuCl/ NaCl (M) | Organics | Duration | Result |
|---|---|---|---|---|
| 8 | 2.2~2.5 constant within 4.5~5.5/ 0.8~1.2/ 2.2~2.5 | Mixture of organics >500 ppm | 9 h | Initial 100%, stable between 97% to 102% during whole experiment |

In experiment Nos. 1, 2, 4, 5, and 6, copper solutions containing organics were prepared according to the listed concentrations. In experiment Nos. 3, 7 and 8, the organics in the system included and not limited to: chloroethanol (CE), ethylene dichloride (EDC), monochloroacetaldehyde (MCA), and dichloroacetaldehyde (DCA). The concentration of the organics ranged from a few ppm to thousands of ppm, and changed over time. The overall concentration was larger than 500 ppm at any given time.

In each experiment in Table I, the measurement step was performed many times during 90 min to 50 h (without any cleaning step). All results were normalized to the first result at the beginning of the test to show the reproducibility. In experiment No. 2, the UME was pre-soaked in CE for 24 h before the test.

In each experiment in Table II, the cleaning step was performed before each measurement step. All results were normalized to the first result at the beginning of the test to show the reproducibility.

In experiments 4-8 (shown in Table II), a set of potential cycles (set X of the one or more potential cycles) were applied to the UME in the cleaning step before the measurement step. For this set of potential cycles (cleaning step), the voltage sweeps were applied to the UME between just below the open circuit potential (OCP) and a higher potential where the UME evolved gas (e.g. Cl$_2$ and O$_2$ in this case). The range of the higher potential sweep can be broader or narrower as long as gas is evolved on the UME surface and the potential does not damage the UME or cause additional adsorption. The aqueous medium was allowed to flow through the UME cell to ensure the removal of gas bubbles from the UME surface. This step strips off any organic/inorganic that may be adsorbed on the UME surface, including and not limited to organic by products.

In all the experiments 1-8 (shown in Table I and II), multiple potential cycles were applied to the UME (set Y of the one or more potential cycles) in the measurement step. The potential of the first step was at the open circuit potential, the potential of the following step was at a higher potential where the rate of reaction was mass transfer (diffusion in this case) limited. These two potential steps were repeated six times to give better accuracy of the measurement. The coefficient of variation in this step was usually within 5% to 10%. The flow was stopped during this step to ensure that the current measured was under diffusion and not convection control.

At the OCP during measurement steps, the solution remained at its initial condition. At higher potential during measurements steps, the UME oxidized the CuCl to CuCl$_2$ at the electrode surface. When a certain potential is applied on the electrode surface, the ions with opposite charge may migrate towards the surface forming a layer, this layer may then attract ions with opposite charge (the same charge with the electrode potential) to form another layer. This double layer may have a capacitance effect when the potential of the electrode changes, causing a spike and gradual decay similar to capacitor discharge. This decay of the curve was fitted to a mathematical equation to measure a steady state current. A correlation curve was then built between Cu(I)Cl concentration by titration method and steady state current measured from UME. The UME current was then translated to Cu(I)Cl concentration using this correlation.

It was observed that when the cleaning step was applied to the UME (Table II), the current stayed stable for extended period of time resulting in stable measurements. However, without the cleaning steps (Table I), the current was not found to be stable and reliable measurements couldn't be made.

What is claimed is:

1. A method to measure concentration of metal ions in presence of one or more organic compounds in an aqueous medium comprising:
   contacting an aqueous medium comprising metal ions and one or more organic compounds with an ultramicroelectrode (UME) in a UME cell;
   cleaning surface of the UME from deposition of the one or more organic compounds by passing a gas on the surface of UME, by forming a gas on the surface of UME, by mechanically cleaning the surface of UME, or combinations thereof;
   subjecting the UME to a set Y of one or more potential cycles causing oxidation of the metal ions in lower oxidation state to a higher oxidation state or causing reduction of the metal ions in higher oxidation state to a lower oxidation state; and
   measuring a steady state current in the UME and calculating the concentration of the metal ions.

2. The method of claim 1, wherein the cleaning of the surface of the UME from the deposition of the one or more organic compounds by forming the gas on the surface of UME comprises subjecting the UME to a set X of one or more potential cycles to form oxygen gas, chlorine gas, hydrogen gas, sulfur dioxide gas, or combinations thereof, on the surface of the UME.

3. The method of claim 2, wherein voltage range of the set X of the one or more potential cycles is higher than reduction potential of the metal ion to prevent reduction of the metal ion and its deposition on the UME surface, wherein the metal ion is iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combinations thereof.

4. The method of claim 2, wherein voltage range of the set X of the one or more potential cycles is ±5V vs Standard Hydrogen Electrode (SHE), ±3V vs SHE, between 0.2V to 2.5V vs SHE, or between 0.6V to 2.5V vs SHE.

5. The method of claim 1, wherein voltage range of the set Y of the one or more potential cycles comprises oxidation or reduction potential of the metal ions or is between open circuit potential of the metal ions and the oxidation or reduction potential of the metal ions, wherein the metal ion is iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combinations thereof.

6. The method of claim 5, wherein the voltage range of the set Y of the one or more potential cycles comprises 0.65-0.85V vs SHE or between open circuit potential and 0.85V vs SHE.

7. The method of claim 1, wherein the cleaning of the surface of the UME from the deposition of the one or more organic compounds by passing the gas on the surface of the UME comprises bubbling a hydrogen gas, bubbling an oxygen gas, bubbling a nitrogen gas, or bubbling a chlorine gas on the surface of the UME.

8. The method of claim 1, wherein concentration of the one or more organic compounds in the aqueous medium is between about 0.5-5000 ppm.

9. The method of claim 1, wherein the one or more organic compounds comprise ethylene dichloride, chloroethanol, monochloroacetaldehyde, dichloroacetaldehyde, trichloroacetaldehyde, or combinations thereof.

10. The method of claim 1, wherein the UME is made of gold, platinum, titanium, carbon, conductive polymer, or iridium.

11. The method of claim 1, wherein the metal ion is iron, copper, tin, chromium, or combination thereof.

12. The method of claim 1, wherein the metal ion is a metal halide.

13. The method of claim 1, wherein the concentration of the metal ions in the lower or the higher oxidation state is more than 0.5M or a total metal ions concentration in the aqueous medium is more than 1M.

14. The method of claim 1, further comprising keeping the UME cell at temperature of between 50-100° C.

15. The method of claim 1, wherein the measurement of the concentration of the metal ions in the lower and/or the higher oxidation state in the aqueous medium is conducted before, during, and/or after administration of the aqueous medium to an anode chamber of an electrochemical cell where the metal ions are oxidized from the lower oxidation state to the higher oxidation state at an anode.

16. The method of claim 1, wherein the measurement of the concentration of the metal ions in the lower and/or the higher oxidation state in the aqueous medium is conducted before, during, and/or after administration of the aqueous medium to a reactor where the metal ions in the higher oxidation state in the aqueous medium are reacted with an unsaturated or saturated hydrocarbon to form one or more organic compounds and the metal ions in the lower oxidation state in the aqueous medium.

17. An ultramicroelectrode (UME) cell, comprising:
a UME cell comprising a UME configured to measure concentration of metal ions in lower and/or higher oxidation state in an aqueous medium comprising one or more organic compounds, wherein the UME cell is configured to subject the UME to a set X of one or more potential cycles to form one or more gases on the surface of the UME and the UME cell is configured to subject the UME to a set Y of one or more potential cycles causing oxidation of the metal ions in lower oxidation state to a higher oxidation state or causing reduction of the metal ions in higher oxidation state to a lower oxidation state.

18. The UME cell of claim 17, further comprising an adsorption unit operably connected to the UME cell comprising an adsorbent configured to adsorb the one or more organic compounds from the aqueous medium.

19. A system configured to measure concentration of metal ions in presence of one or more organic compounds in an aqueous medium comprising: a UME cell comprising a UME configured to measure concentration of metal ions in an aqueous medium comprising one or more organic compounds; and the aqueous medium comprising metal ions and the one or more organic compounds,
wherein the UME cell is configured to subject the UME to a set X of one or more potential cycles to form one or more gases on the surface of the UME and the UME cell is configured to subject the UME to a set Y of one or more potential cycles causing oxidation of the metal ions in lower oxidation state to a higher oxidation state or causing reduction of the metal ions in higher oxidation state to a lower oxidation state.

20. The system of claim 19, wherein the one or more gases comprise oxygen gas, chlorine gas, hydrogen gas, sulfur dioxide gas, or combinations thereof.

* * * * *